(12) United States Patent
Barnes

(10) Patent No.: US 10,113,984 B2
(45) Date of Patent: Oct. 30, 2018

(54) INTEGRATED EPR NMR WITH FREQUENCY AGILE GYROTRON

(71) Applicant: WASHINGTON UNIVERSITY, St. Louis, MO (US)

(72) Inventor: Alexander B. Barnes, St. Louis, MO (US)

(73) Assignee: Washington University, St. Louis, MO (US)

(*) Notice: Subject to any disclaimer, the term of this patent is extended or adjusted under 35 U.S.C. 154(b) by 165 days.

(21) Appl. No.: 15/310,509

(22) PCT Filed: May 12, 2015

(86) PCT No.: PCT/US2015/030333
§ 371 (c)(1),
(2) Date: Nov. 11, 2016

(87) PCT Pub. No.: WO2015/175507
PCT Pub. Date: Nov. 19, 2015

(65) Prior Publication Data
US 2017/0074811 A1 Mar. 16, 2017

Related U.S. Application Data

(60) Provisional application No. 61/993,595, filed on May 15, 2014.

(51) Int. Cl.
*G01R 33/62* (2006.01)
*G01N 24/12* (2006.01)
*G01R 33/60* (2006.01)
*G01R 33/28* (2006.01)
*G01R 33/30* (2006.01)
*G01R 33/31* (2006.01)
*G01R 33/345* (2006.01)

(52) U.S. Cl.
CPC .......... *G01N 24/12* (2013.01); *G01R 33/282* (2013.01); *G01R 33/307* (2013.01); *G01R 33/60* (2013.01); *G01R 33/62* (2013.01); *G01R 33/31* (2013.01); *G01R 33/345* (2013.01)

(58) Field of Classification Search
CPC ..... G01R 33/62; G01R 33/282; G01R 33/307
See application file for complete search history.

(56) References Cited

U.S. PATENT DOCUMENTS

| 5,166,620 | A | 11/1992 | Panosh |
| 6,191,724 | B1 | 2/2001 | McEwan |
| 2005/0107696 | A1* | 5/2005 | Griffin ................. C07D 409/14 600/431 |

(Continued)

OTHER PUBLICATIONS

International Search Report and Written Opinion of International Application No. PCT/US2015/030333, dated Aug. 27, 2015, 7 pages.

(Continued)

*Primary Examiner* — Jermele M Hollington
*Assistant Examiner* — Alvaro Fortich
(74) *Attorney, Agent, or Firm* — Armstrong Teasdale LLP

(57) ABSTRACT

A frequency agile gyrotron for use in combination with an NMR system is disclosed. The frequency agile gyrotron combined with EPR-NMR magic angle spinning resonators and cryogenic sample cooling may increase the sensitivity of solid state NMR with DNP.

14 Claims, 22 Drawing Sheets

(56) References Cited

U.S. PATENT DOCUMENTS

2006/0181381 A1* 8/2006 Markiewicz ....... G01R 33/3875
335/216
2012/0176133 A1* 7/2012 Sirigiri ................. G01R 33/282
324/318
2014/0068962 A1 3/2014 Mori et al.

OTHER PUBLICATIONS

Kuleshov, O. et al., Development of Feedback Control Scheme for the Stabilization of Gyrotron Output Power, FIR Center Report, Nov. 2012, 15 pages.
Jawla, S. et al., Continuously Tunable GHz Gyrotron with a Double Disk Window for DNP-NMR Spectroscopy, J Infrared Milli Terahz Waves, 2013, 6 pages.

* cited by examiner

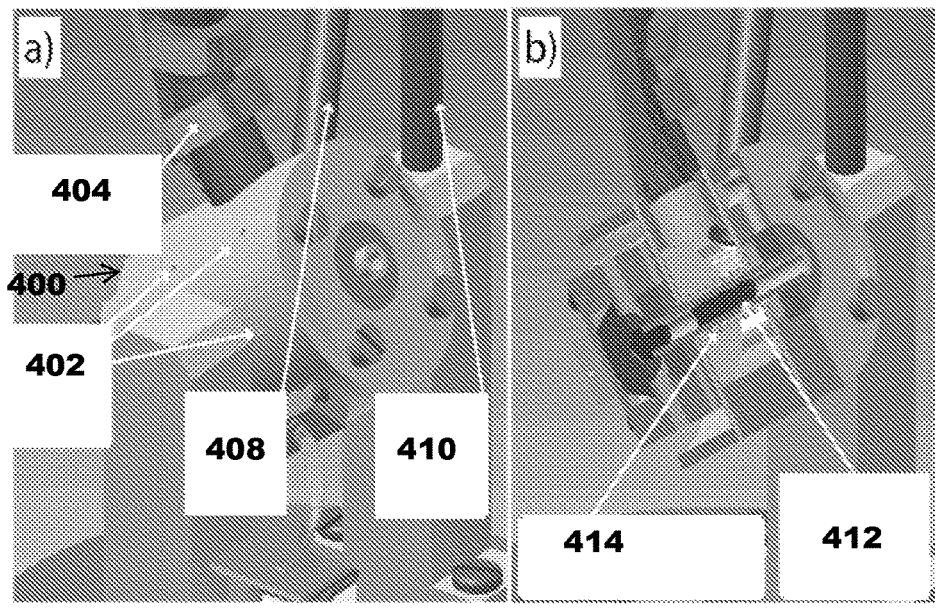
FIG. 4A  FIG. 4B
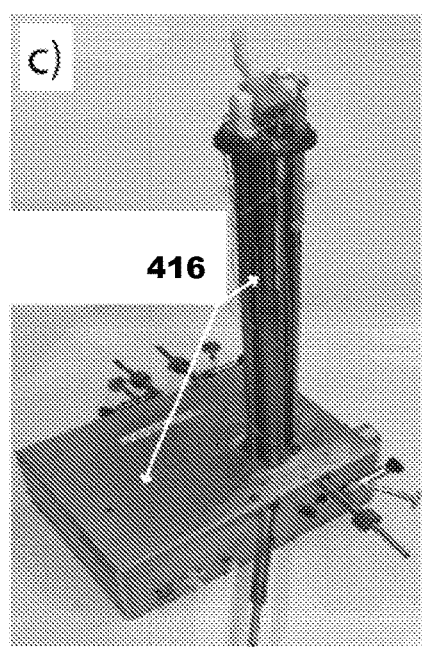 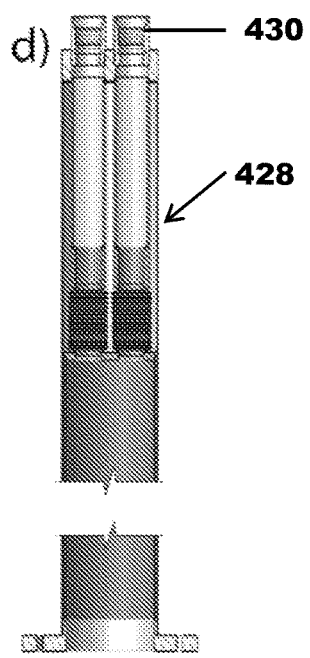
FIG. 4C  FIG. 4D

INTEGRATED EPR NMR WITH FREQUENCY AGILE GYROTRON

CROSS-REFERENCE TO RELATED APPLICATIONS

This application is a PCT application claiming the benefit of U.S. Provisional Application No. 61/993,595, filed on May 15, 2014, which is hereby incorporated by reference herein in its entirety.

FIELD OF THE INVENTION

The present invention relates to frequency agile gyrotrons used to improve magnetic resonance experiments.

BACKGROUND

Dynamic Nuclear Polarization (DNP) has emerged as a powerful strategy to increase the sensitivity of NMR experiments on a wide range of biological systems by transferring the large polarization of electron spins (EPR) to nuclear spins (NMR). Crucial to the successful implementation of DNP in conjunction with magic angle spinning (MAS) has been the development of gyrotrons and NMR probes, instrumentation used to perform DNP. DNP currently enhances the sensitivity of NMR experiments on membrane proteins by a factor of about 50 and on model systems up to about 120 at 9 Tesla.

The larger gyromagnetic ratio of electron spins compared to proton spins, lower temperatures, and faster recycle delays all combine to potentially increase the NMR sensitivity by a factor of 360,000. The associated experimental averaging time may decrease by a factor of 133 billion. Transferring 100% of the polarization from the electron spins and cooling samples to 5 K to achieve the theoretical gains poses an ongoing challenge.

The microwave source (usually a gyrotron) used in contemporary DNP experiments is left locked on the same frequency for continuous-wave operation during the entire experiment. This is because although DNP gyrotrons have high microwave power output levels (>10 W), they have not yet been tuned on a fast timescale in existing magnetic resonance experiments.

Current MAS DNP technology may experience difficulty achieving sufficient control of EPR spins. Only a fraction of the 1 GHz broad nitroxide lineshape can be covered with a non-tunable 1 MHz γB1 microwave field of about 200 GHz that exerts control over the EPR spins. Others have not been able to use EPR spin labels on peptides for DNP because of extensive paramagnetic broadening. Therefore, there is a need for a frequency agile gyrotron microwave source that can output short pulses to not only sweep-through the EPR linewidth, but also to control all of the EPR spins simultaneously with a broad excitation bandwidth. At the same time, there is a need to increase the γB1 microwave field strength by about 3 orders of magnitude (from about 1 MHz to about 1 GHz).

SUMMARY

In various aspects of the disclosure, a frequency agile gyrotron system for DNP NMR is provided that includes: an NMR spectrometer; a signal processor operatively connected to the NMR spectrometer; and a frequency agile gyrotron operatively coupled to the NMR spectrometer and to the signal processor. The signal processor receives one or more voltages from the NMR spectrometer and produces a control signal. The frequency agile gyrotron is configured to emit a broad-banded microwave output that includes a gyrotron bandwidth. The NMR spectrometer controls a frequency of the broad-banded microwave output via the control signal. The frequency agile gyrotron responds to the control signal on a timescale of microseconds. The gyrotron bandwidth is wider than an EPR linewidth and an NMR frequency.

The bandwidth of the frequency agile gyrotron may be between about 10 MHz and about 1000 MHz. The NMR spectrometer may further include a magnetron injection gun that includes a cathode and an anode. The one or more voltages from the NMR spectrometer are chosen from at least one of: a cathode voltage, an anode voltage, and an acceleration voltage comprising a voltage difference between the cathode voltage and the anode voltage. The frequency agile gyrotron may be operated as a backward wave oscillator. The frequency agile gyrotron may produce the broad-banded microwave output at a phase and frequency stable condition, and the broad-banded microwave output may be sliced or gated to provide at least one of: a wide instantaneous bandwidth that includes short pulses on a nanosecond scale and an adjustable power transmission length for phase control. The NMR spectrometer may further include a combined EPR-NMR magic angle spinning resonator. The system may further include a helium cooling system for cooling a sample to below about 5 to about 60 Kelvin with helium using a spinning MAS rotor as a centrifugal gas compressor.

In another aspect, a method of DNP NMR using a frequency agile gyrotron system that includes an NMR spectrometer operatively coupled to a frequency agile gyrotron is provided. The method includes controlling an output frequency of a broad-banded microwave output produced by the frequency agile gyrotron by changing an operational voltage of the frequency agile gyrotron in response to a control signal corresponding to at least one voltage received from a magnetron injection gun of the NMR spectrometer. The at least one voltage may be chosen from: a cathode voltage, an anode voltage, and an acceleration voltage that is a voltage difference between the cathode voltage and the anode voltage. Controlling the output frequency of the broad-banded microwave output produced by the frequency agile gyrotron may include at least one of: sweeping the output frequency on a timescale ranging from nanoseconds to microseconds; producing the broad-banded microwave output in short pulses; and producing the broad-banded microwave output in a phase and frequency stable form and gating the broad-banded microwave output with at least one nanosecond scale switches. The method may further include at least one of: performing at least one time-domain DNP transfer; transferring polarization from electrons to a nucleus using hyperfine couplings of greater than 10 KHz; decoupling an electron spin from a nuclear spin; and manipulating EPR spins during magic angle spinning NMR and EPR experiments to measure EPR to NMR distances and orientations. The operational voltage of the frequency agile gyrotron may be changed on a timescale ranging from nanoseconds to microseconds to perform the at least one time-domain DNP transfer. The at least one time-domain DNP transfer may be accomplished using at least one transfer mechanism chosen from: integrated solid effect, a nuclear orientation via electron spin locking, and an electron nuclear cross polarization. The method may further include cooling a sample to below about 5 to about 60 Kelvin with helium using a spinning MAS rotor as a centrifugal gas compressor.

BRIEF DESCRIPTION OF THE DRAWINGS

The following figures illustrate various aspects of the disclosure.

FIGS. 4A, 4B, 4C, 4D, 4E, 4F, and 4G are schematic representations of NMR DNP probe instrumentation.

FIG. 5A is a stepped voltage and frequency switching scheme. FIG. 5B is a stepped and sinusoidal modulation scheme superimposed. FIG. 5C is a saw-toothed function scheme. FIG. 5D is a sinusoidal modulation from an alternating (AC) current radio frequency circuit scheme. FIG. 5E is a tangential envelope for adiabatic passage scheme. FIG. 5F is a stochastic voltage and frequency modulation scheme.

FIG. 13A illustrates TOTAPOL. FIG. 13B illustrates water soluble BDPA. FIG. 13C illustrates nitroxide spin labels, TAOC and MTSSL (left) and chelated gadolinium (right).

Corresponding reference characters and labels indicate corresponding elements among the views of the drawings. The headings used in the figures should not be interpreted to limit the scope of the claims.

DETAILED DESCRIPTION

Figure 1:
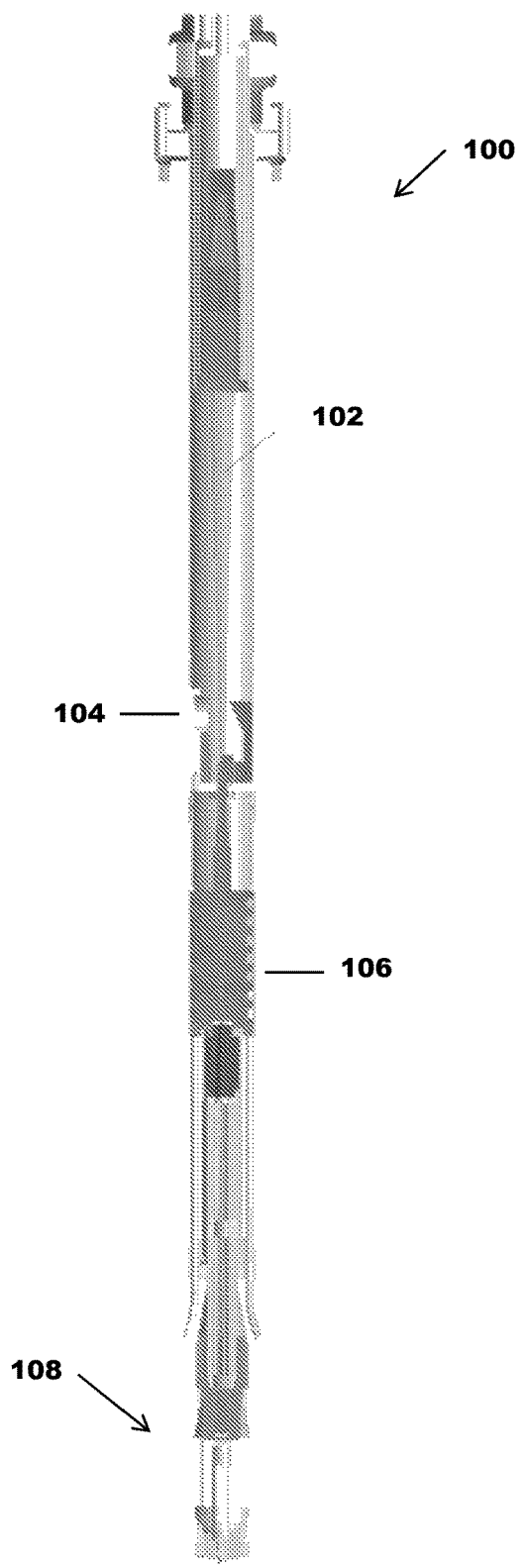
FIG. 1 is an illustration of a 197 GHz high-power gyrotron oscillator for frequency-agile DNP.

NMR spectroscopy currently does not utilize higher dimension spectra to yield better resolution primarily because of the sensitivity required to record each additional dimension. A frequency agile gyrotron may provide the sensitivity and instrumentation to overcome these limitations.

A frequency agile gyrotron (or a backward wave oscillator, BWO) microwave source that can output short pulses may allow not only to sweep-through the EPR linewidth, but also to control all of the EPR spins simultaneously with a broad excitation bandwidth. At the same time, the γB1 microwave field strength may be increased by 3 orders of magnitude (from about 1 MHz to about 1 GHz). Higher power output from the frequency agile gyrotrons and an EPR resonator with a quality factor of about 100 will yield an about 1 GHz γB1 and enhanced control of the 1 GHz broad nitroxide EPR resonance. To take advantage of the new EPR control, cryogenic operation may be required to extend electron spin coherence lifetimes. In an aspect, the sample may be cooled to about 27 K. The system may include a miniature closed loop helium cooling apparatus that uses the spinning sample rotor as a centrifugal helium compressor. Cryogenic and THz technology may be able to utilize mounted EPR spin labels to simultaneously measure multiple long-range (50±0.2 Å) electron nuclear distances.

Gyrotron oscillators, or backward wave oscillators, can have a sufficient frequency and phase stability to provide a stable microwave beam. The beam can then be sliced and manipulated with already established semiconductor light activated switches to yield nanosecond scale pulses (GHz scale bandwidth), and also phase control by means of adjustable power transmission lengths.

Provided herein is a frequency agile gyrotron system for use in DNP NMR or combined EPR-NMR. The frequency agile gyrotron system may include a broadband gyrotron microwave source, combined EPR-NMR magic angle spinning resonators, and extreme cryogenic sample cooling to increase the sensitivity of solid state Nuclear Magnetic Resonance (NMR) experiments by a factor of 20,000 with novel time-domain Dynamic Nuclear Polarization (DNP). This tremendous boost in sensitivity and control of EPR spins may result in acquiring data six orders of magnitude faster than conventional NMR and may permit multiple simultaneous electron-nuclear distances measurements out to 50 Å. The applications of this technology development and structure determination methodology may have applications to proteins, molecules, and chemical architectures of structural interest.

A gyrotron with frequency agility may be tuned by changing the operating voltage. Although it is possible to change the gyrotron frequency by changing the operating magnetic field; such a method is not amenable to fast tuning schemes due to the significant inductance of the gyrotron magnet. The same magnetic tuning previously seen in DNP gyrotrons can also be accomplished with voltage tuning. However, a 460 GHz gyrotron for 700 MHz DNP experiments does not have enough power (>10 W) over the entire nitroxide EPR lineshape (~1.8 GHz broad at 16.4 Tesla, or 700 MHz 1H). Exert control over all of the electron spins with a strong microwave field enables enhanced control the DNP Hamiltonian and improved DNP performance.

The frequency agile gyrotron may have the ability to change the voltage and gyrotron frequency on a timescale ranging from nanoseconds to microseconds, which may improve DNP and magnetic resonance spectroscopy. Electron decoupling may be used with the frequency agile gyrotron, which is analogous to proton decoupling. In addition, the frequency agile gyrotron may enable Electron Dephased Rotational Echo Double Resonance (ED-RE-DOR), which is analogous to classical nuclear spin dephased REDOR. The ability to control the microwave irradiation frequency of gyrotrons during DNP may allow significantly more control over the DNP Hamiltonian. As a result, beneficial interactions may be turned on and detrimental ones turned off, resulting in significantly improved performance. DNP can routinely provide substantial sensitivity gains, but there are still tremendous opportunities for advancements. Frequency-agile gyrotrons can overcome many of the current limitations of DNP including: 1) Poor performance at temperatures higher than 100 K; 2) Inhomogenous line-broadening; 3) Inverse scaling enhancements with magnetic field; 4) Paramagnetic broadening; 5) Failure at MAS frequencies >~8 KHz; and 6) Disperse polarization.

Electron-nuclear Decoupling in DNP

Dynamic nuclear polarization (DNP) may increase the sensitivity of NMR experiments on a wide range of biological systems. The sensitivity of DNP experiments is generated from transferring the large polarization (sensitivity) in the electron paramagnetic resonance (EPR) spin reservoir to nuclear spins. Strong hyperfine couplings yield fast and efficient electron to nuclear polarization transfer. However, nuclear spins with strong hyperfine couplings suffer from extensive paramagnetic broadening. The method of DNP NMR with a frequency agile gyrotron may first utilize strong hyperfine couplings to transfer polarization, and then switch on a strong electron-decoupling field. The pulse sequence in FIG. 8B implements a DNP polarization ($\omega$DNP) period followed by hyperfine decoupling ($\omega$Decouple). This allows close-in nuclei to quickly become polarized, followed by a period of hyperfine decoupling that permits spectroscopy on the close-in $^{13}C$ spins on a protein and any bound ligands.

Electron spins on stable organic radicals interact with the magnetic field 657 times stronger than $^1H$ nuclear spins, resulting in a theoretical maximum gain in sensitivity of a factor of 657 as illustrated in the equation of polarization (Eqn. (I)) below. The decreasing sensitivity of NMR experiments on biomedically relevant preparations may be compensated for with drastic gains in sensitivity provided by transferring polarization from electron to nuclear spins (DNP), cooling samples to about 27 Kelvin, and repeating experiments faster by utilizing the short relaxation time of electron spins.

Eqn. (I)

Gains in Sensitivity from Proposed NMR Development

| | DNP | gain in polarization with temperature | reduction in recycle delay | total gain in sensitivity | total gain in time |
|---|---|---|---|---|---|
| theoretical limits | → 657 | $\frac{273K}{5K}$ = 55 | $\left(\frac{3s}{30ms}\right)^{1/2}$ = 10 | → 360,000 → | 1.3 x 10$^{11}$ (133 billion) |
| expected gains | → 500 | $\frac{273K}{27K}$ = 10 | $\left(\frac{3s}{200ms}\right)^{1/2}$ = 4 | → 20,000 → | 4.0 x 10$^8$ (400 million) |
| expression for polarization (sensitivity) | → P = | $\frac{-\gamma \hbar B_O}{2k_B T}$ | → | $\gamma$;high gyromagnetic ratio of electrons leveraged for DNP T;lower temperature yields higher sensitivity | |

In biomedically relevant NMR samples, the electron to nuclear DNP sensitivity transfer works efficiently only at temperatures below about 100 K. Such cryogenic temperatures also inherently boost NMR sensitivity by increasing the population of spins occupying the lower energy level—note that temperature is a denominator in Eqn. (I). These two enhancement effects are multiplicative, meaning the experimentally realistic gain in NMR sensitivity for DNP experiments performed at 27 Kelvin is a factor of 5000 (or 2.5×10$^7$ in time). Yet another advantage to the use of DNP in NMR experiments is that the recycle delay between NMR scans is governed by the relaxation properties of the electron spins, which is much faster than nuclear spins, and can result in 100 times faster experimental averaging.

In an aspect, DNP may enhance the sensitivity of NMR experiments on membrane proteins by a factor of about 50. Electron nuclear decoupling experiments employed with a frequency agile gyrotron (see FIG. 1) may improve DNP enhancement factors to 500, while also reducing the recycle delays from about 3 seconds to 300 milliseconds. Advanced helium cooled NMR probe instrumentation may permit NMR experiments at temperatures as low as about 27 K, resulting in a sensitivity gain of about a factor of 20,000 and a data collection rate about 400 million times faster than conventional solid state NMR.

Figure 2A:
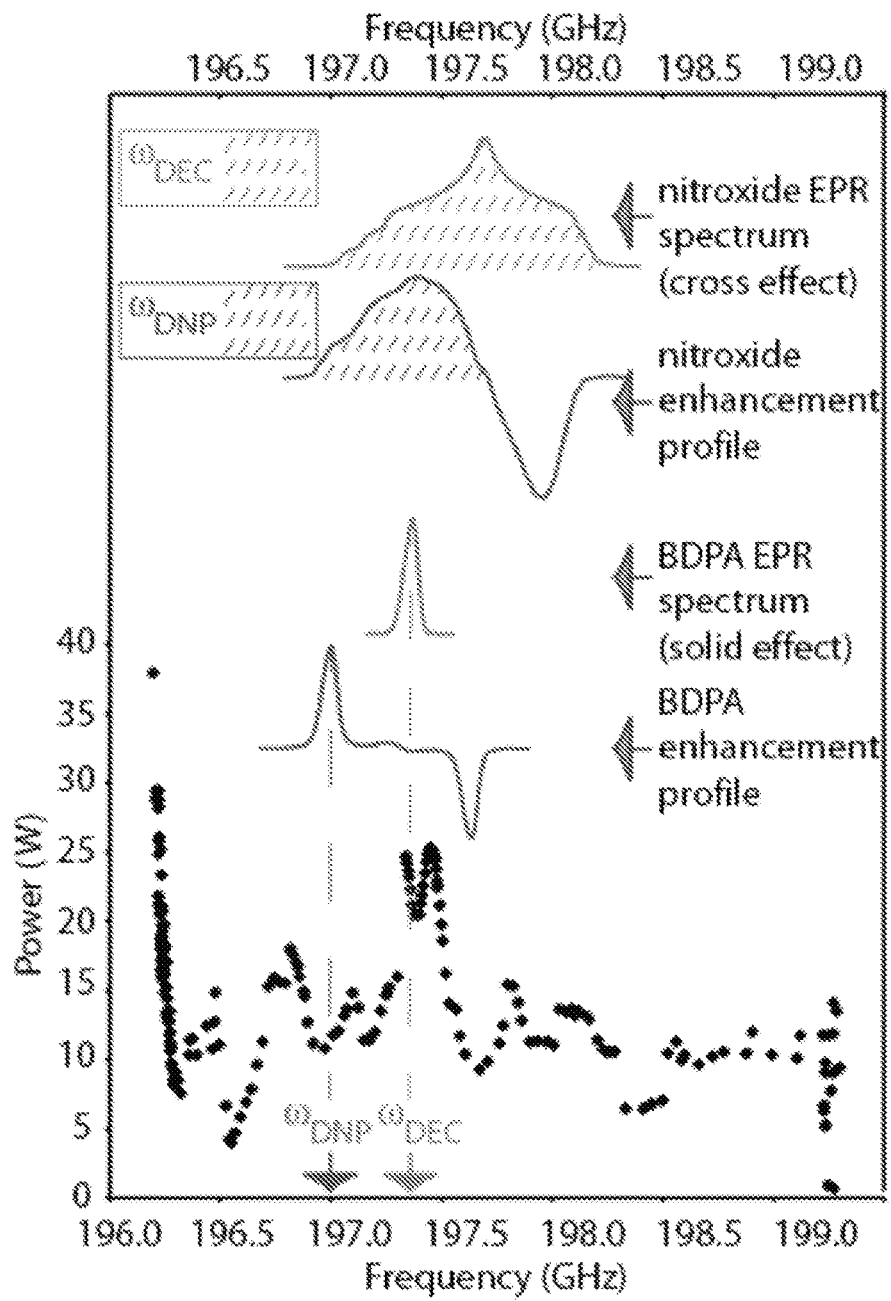
FIG. 2A is projected nitroxide and BDPA EPR lineshapes and DNP enhancement profiles overlaid on projected power vs. frequency plot (from a 250 GHz gyrotron). Decoupling frequencies are marked as $\omega_{DEC}$ and enhancement frequencies are marked as $\omega_{DNP}$.
Figure 2B:
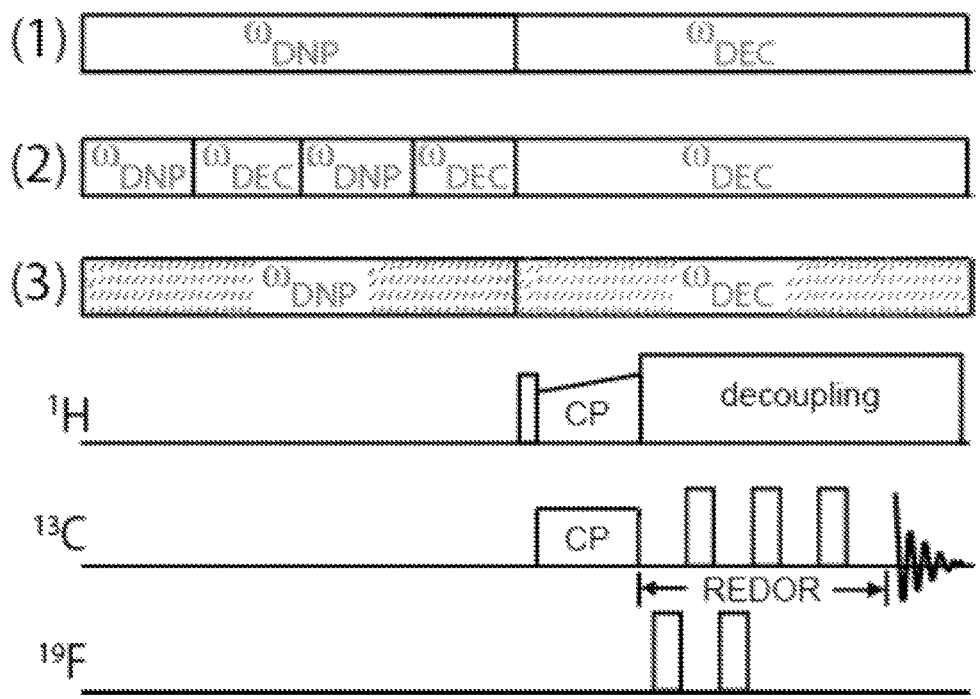
FIG. 2B shows pulse sequence schemes achievable with a frequency agile gyrotron. Electron-nuclear decoupling and frequency modulation of the gyrotron output frequency will enable improvements in DNP performance.

The successful implementation of DNP in conjunction with magic angle spinning (MAS) for biomolecular structure determination has been enabled by the development of gyrotrons and NMR probes. However, gyrotrons that can switch the microwave frequency quickly have not yet been employed in DNP experiments. By switching the gyrotron frequency from 197.0 GHz to 197.3 GHz on a timescale of microseconds, the EPR spins may be irradiated and partially average out the electron-nuclear dipolar interactions with an about 2 MHz continuous microwave decoupling field (FIG. 2A). This frequency jump may be achieved by decreasing the operating voltage of the gyrotron by about 670 V. Decoupling the electron spins during the NMR acquisition (FIG. 2B, scheme 1) may improve sensitivity, since many NMR signals are extinguished due to direct interactions with the EPR spins (paramagnetic relaxation effects). Decoupling the electron spins may further have an impact on the NMR spectroscopy that can be performed on nuclear spins that otherwise suffer from extensive paramagnetic broadening.

The strong electron-nuclear dipolar interaction not only broadens NMR spectra, but also creates a so-called spin diffusion barrier. This barrier to nuclear polarization dispersion exists because strong electronuclear dipolar couplings shift the resonances of the protons close into the polarizing agent too far in frequency from resonances from "bulk" protons. The spin diffusion barrier is detrimental to DNP performance for two reasons. The close-in protons actually drain the polarization from the electron, hindering that polarization from getting to the bulk spins. In addition, the very strong electron-nuclear dipolar couplings cannot be leveraged for DNP. The couplings of up to 7 MHz yield fast and efficient DNP transfers of polarization from the electron.

Those strong couplings may be utilized and in turn permit DNP at physiological temperatures and higher spinning frequencies, and also improve DNP enhancements at cryogenic temperatures. The pulse sequence in FIG. 2B, scheme 2, implements switched polarization ($\omega$DNP) and decoupling ($\omega$DEC) periods. This enables close-in protons to quickly become polarized, followed by a time when the $\omega$DEC field collapses the spin diffusion barrier to allow the polarization to be efficiently spread to the bulk. Electron-nuclear decoupling and frequency modulation of the gyrotron output frequency enables drastic improvements in DNP performance.

DNP experiments on membrane proteins have previously used exogenous biradical EPR polarizing agents. Due to the about 100 Å physical separation between these EPR spins to the nuclear spins of structural interest, the enhanced EPR polarization must undergo an inefficient relayed polarization transfer. In an aspect, the $^{13}$C spins may be polarized directly with rigid amide nitroxide residues incorporated into the protein domains.

In an aspect, similar to the orientation of the biradicals in exogenous EPR polarizing agents, rigid peptide amide nitroxides must have an orthogonal orientation of the two g-tensors. In this aspect, the 90° orientation of the amide radicals in FIG. 9C may yield a separation of EPR frequencies that match the $^{13}$C Larmor frequency (75 MHz) and thus polarize nuclear spins effectively. Solid phase peptide synthesis may allow incorporation of nitroxide residues and selective labeling of $^{13}$C sites that may be important to ligand binding.

Typically, resolution is compromised due to uniform $^{13}$C labeling and inhomogenous broadening of cryogenic MAS experiments. In an aspect, the method may not require uniform $^{13}$C labeling. Isotope labels may only be used on sites that encode important structural information on ligand binding, such as but not limited to $^{13}$C on Trp252, Leu251, Met239, bryostatin and prostratin. In FIG. 9A, many of the 27 predicted correlation peaks may be resolved in the $^{13}$C-$^{13}$C 2D NMR spectrum. The linewidth (1 ppm) of the predicted resonances in FIG. 9A comes from MAS DNP spectra found in FIG. 8A. $^{13}$C-$^{13}$C correlations peaks are often inhomogenously broadened in DNP spectra due to the cryogenic trapping of multiple conformations. However, each distinct conformation is characterized by correlated chemical shifts that can be exploited to increase spectral resolution with a double quantum correlation in the indirect $^{13}$C dimension. Such line-narrowing strategies have not yet been employed to structure determination efforts of membrane proteins with MAS DNP.

Time Domain DNP Transfers with Frequency Swept or Broadband Gyrotron Oscillators A phenomenon referred to as the Cross Effect is active when the EPR lineshape is wider than the nuclear Zeeman frequency. This is the case for nitroxide radicals. For example the about 1000 MHz lineshape of the nitroxide EPR spectrum shown in FIG. 2A is greater than the corresponding 300 MHz proton frequency. The Cross Effect can be understood in a cross-relaxation framework. When the microwave frequency is targeted on the low-frequency side (about 197.3 GHz in FIG. 2A), the microwaves burn a hole in the mostly inhomogenously broadened EPR spectrum. In other words, the Zeeman spin states of the electron spins near the irradiation frequency become nearly equal. When these spins relax back to their equilibrium Zeeman population, they cross-relax another electron spin on the other side of the EPR lineshape along with a nuclear spin. These nuclear spin states than become polarized according to the Boltzmann distribution of the electron spin states, resulting in DNP enhancements of the NMR sensitivity.

The amount of the EPR spectrum that is saturated from the microwave field is thus an important factor in Cross Effect DNP. If fewer electron spins are saturated, fewer spins participate in DNP and the enhancements are smaller. It follows that a strategy that increases the saturation bandwidth of the microwave field would lead to higher DNP enhancements. A fast (>10 KHz) frequency modulation of the gyrotron frequency, with sufficient microwave power, will accomplish this. Modulating the microwave frequency over the lower frequency side of the EPR spectrum may (shading in FIG. 2A) result in more nuclear polarization and NMR sensitivity.

Time domain DNP transfers such as the Integrated Solid Effect (ISE), Nuclear Orientation via Electron Spin Locking (NOVEL), electron nuclear cross polarization, and other irradiations schemes have been proven to yield fast, efficient transfers at low (~9 GHz) microwave frequencies. All of these techniques could be extended to operate at higher frequencies (100-1000 GHz) with the use of frequency swept gyrotrons (or BWOs), or frequency and phase stable gyrotrons (or BWOs) that supply a microwave beam that can be sliced and manipulated with light activated semiconductors switches. All of these time domain schemes have the possibility of transferring polarization from electrons to nuclei fast enough to allow Optical Polarized DNP at high magnetic fields, and to perform EPR to NMR polarization transfers efficiently at temperatures >200 Kelvin.

Simultaneous EPR-NMR Distance Measurements Up to 50 Å

A $1/r^3$ distance dependence of the dipolar interaction encodes biomolecular structure (see FIG. 9A). Although homonuclear dipolar couplings (labelled $^{13}$C-$^{13}$C in FIG. 9A) can be determined precisely to measure short-range distances, longer distances are more challenging to measure due to the weak nuclear-nuclear dipolar interaction. The electron-nuclear (hyperfine) interaction is 2600 times stronger due to the large magnetic moment of the electron spin. Strong hyperfine couplings may be used to measure electron-nuclear distances on a protein out to about 50 Å.

Figure 8A:
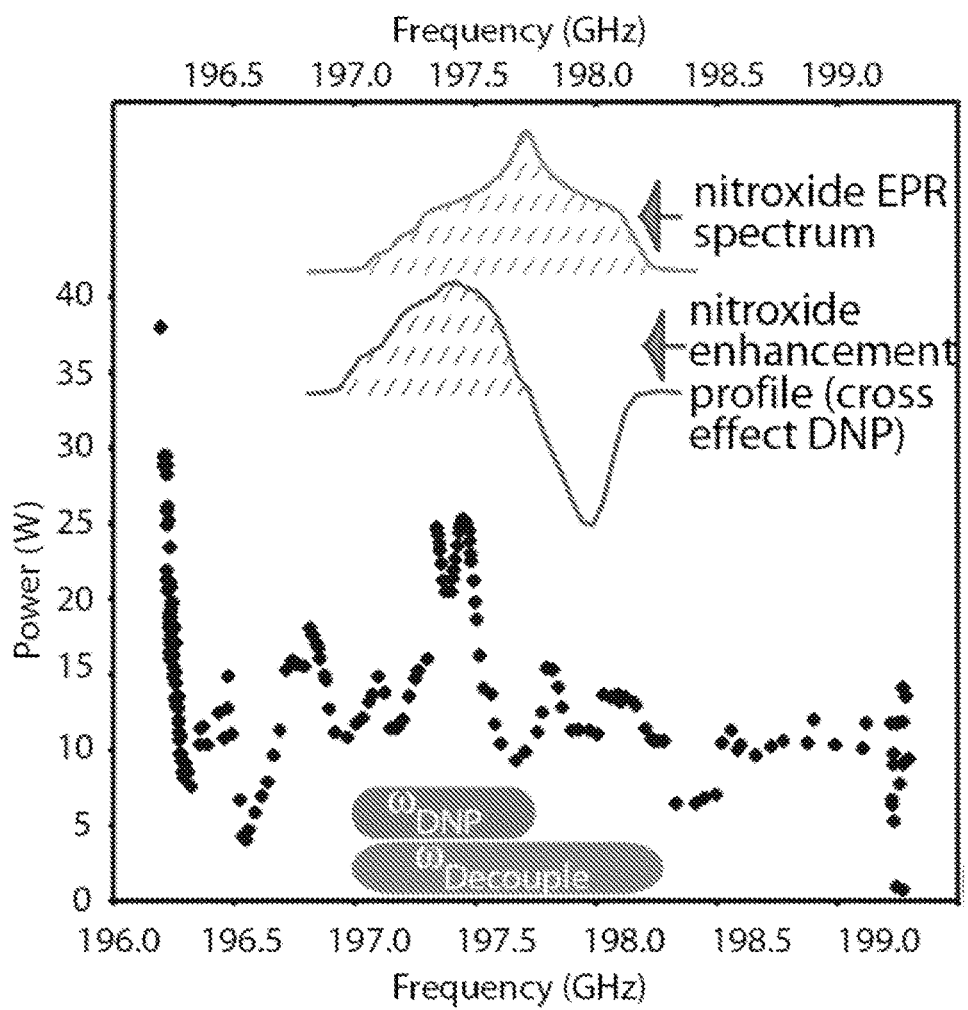
FIG. 8A is a projected nitroxide EPR lineshape and DNP enhancement profile overlaid on a projected power spectrum of the tunable gyrotron.
Figure 8B:
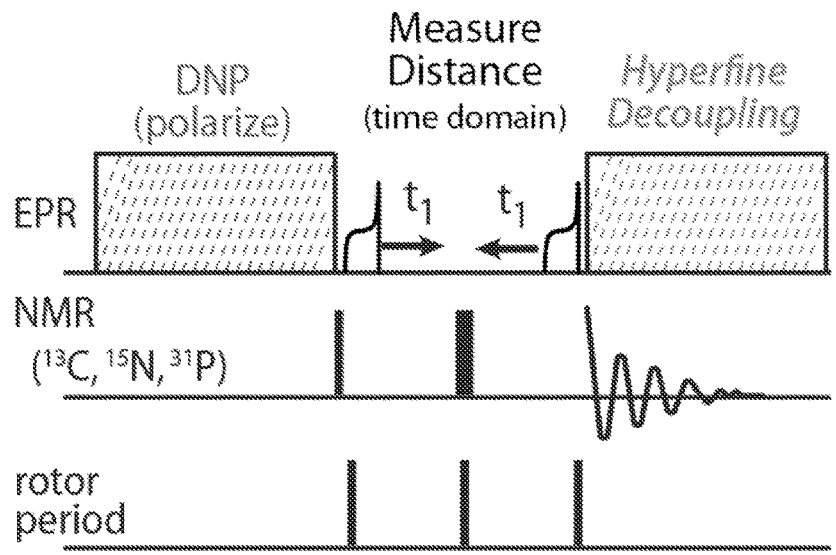
FIG. 8B shows a scheme using frequency modulated MW power (marked DNP) to transfer EPR polarization efficiently to nuclei followed by adiabatic EPR inversions to measure long-range electron-nuclear distances and hyperfine decoupling during NMR signal acquisition.
Figure 9A:
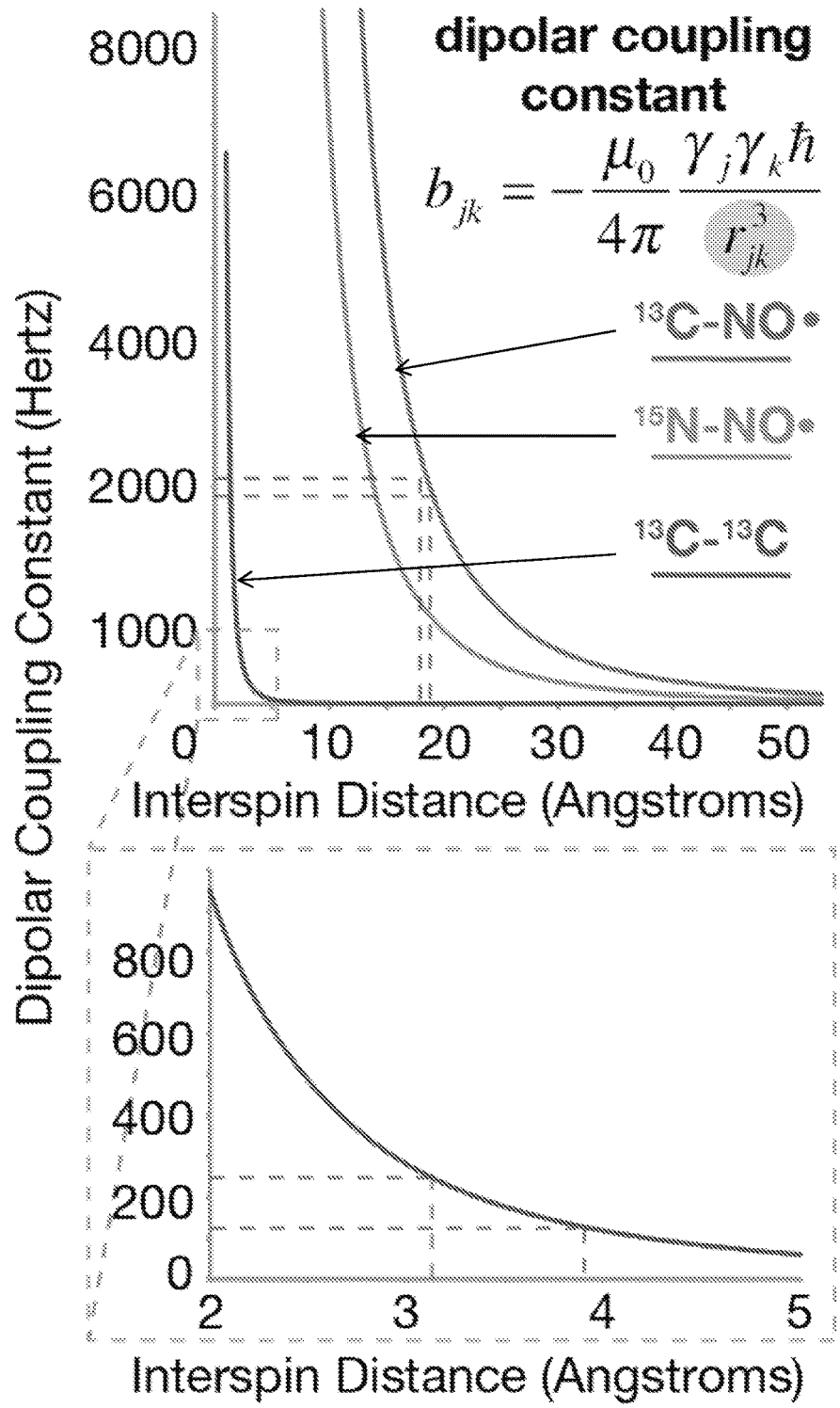
FIG. 9A is a graph of strong hyperfine couplings that may enable long-range distance measurements (top) compared to weak $^{13}C$-$^{13}C$ couplings (bottom).

FIG. 8A illustrates the projected nitroxide EPR lineshape and DNP enhancement profiles overlaid on the projected power spectrum of the frequency agile gyrotron. This experiment may employs electron dephased rotational Hahn-echoes and adiabatic inversions of the electron spin only made possible with frequency agile gyrotron technology disclosed herein. FIG. 8B shows a scheme in which frequency modulated MW power (labeled DNP) transfers EPR polarization efficiently to nuclei, followed by adiabatic EPR inversions to measure long-range electron-nuclear distances and hyperfine decoupling during NMR acquisition.

Figure 9B:
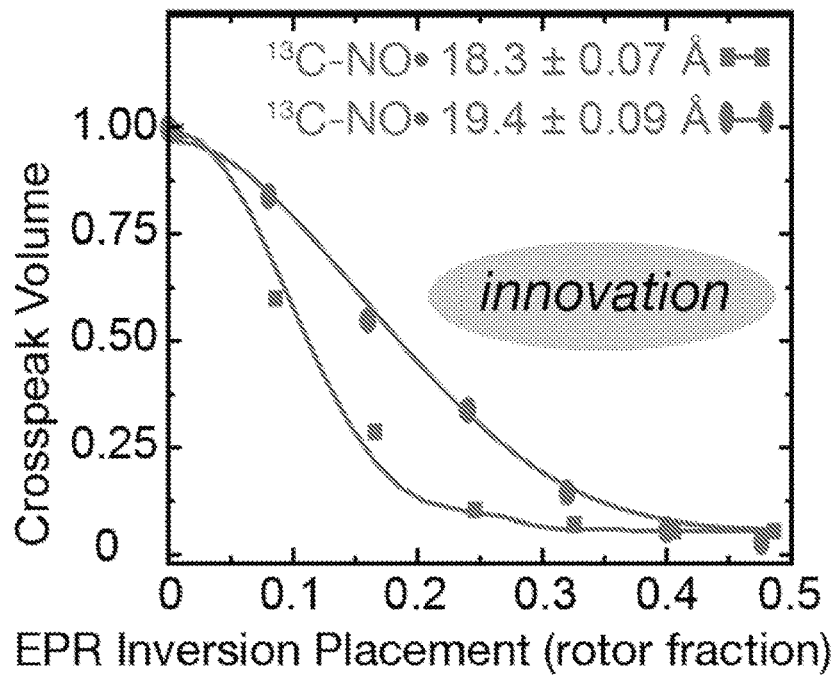
FIG. 9B shows the dephasing of rotational Hahn-echoes with rotor synchronized adiabatic EPR inversions that may yield curves that can be fit to precise long-range distances.
Figure 9C:
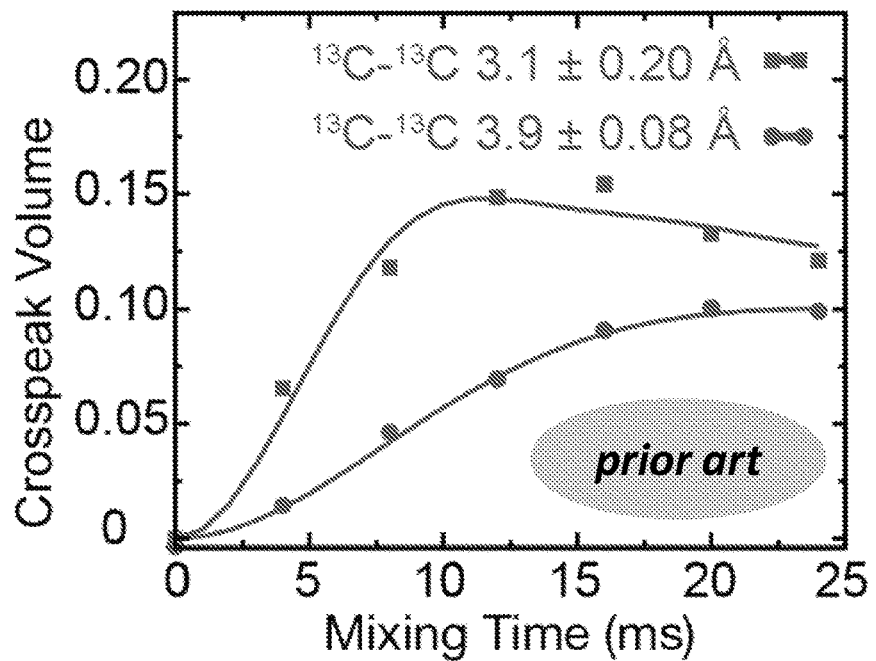
FIG. 9C shows similar curves can be fit to yield precise $^{13}C$-$^{13}C$ distances, but only out to about 5 Å.

Similar to heteronuclear distance measurements, the dephasing of rotational Hahn-echoes may be monitored as a function of the EPR adiabatic inversion placement in the MAS rotor cycle. FIG. 9A shows strong hyperfine couplings may enable long-range distance measurements (see top graph) compared to weak $^{13}C$-$^{13}C$ couplings (see bottom graph). FIG. 9B is a curve fit to precise long-range distances yielded by the dephasing of rotational Hahn-echoes with rotor synchronized adiabatic EPR inversions as disclosed herein. As seen in FIG. 9C, similar curves may be fit to yield precise $^{13}C$-$^{13}C$ distances, but only out to about 5 Å. Due to the strength of the hyperfine interaction, it may be possible to measure the 15-20 Å distances as indicated in FIG. 9A. In an aspect, long-range distances may be measured between rigid nitroxide labels and $^{13}C$ labels both on residues in binding pockets and on ligands with a ±0.2 Å precision.

In an aspect, the transverse electron relaxation may be extended to enable adiabatic EPR inversions. This may be accomplished with deuteration of residues near the nitroxide moiety and by cooling the sample as cold as possible. In one aspect, the sample may be cooled to a temperature less than about 27 Kelvin.

Microwave Frequency Modulation for Broad-banded Electron-Nuclear Decoupling

Extending the decoupling strategies discussed herein above to DNP using nitroxide radicals and the 3-spin Cross Effect mechanism may require a frequency modulation of the microwaves across the entire broad EPR lineshape. Such modulation of the microwave frequency from about 197.0 to 198.3 GHz (see shading in top of FIG. 2A) may be accomplished by modulating the operating voltage of the gyrotron by ±1.4 kV. Continuous waveforms applied in NMR may have similar analogies to EPR and DNP transitions. Analogous to the first heteronuclear decoupling experiments, a random modulation of MW frequency over the lineshape might better average out electron-nuclear couplings.

Magic Angle Spinning (MAS) Solid State NMR

The NMR Hamiltonian contains anisotropic terms such as dipolar interactions and chemical shift anisotropy that can lead to short relaxation times and line broadening in NMR spectra of solid state samples. However, a factor of (3 $\cos^2\theta$−1) in these Hamiltonians allows effectively averaging weaker anisotropic interactions to zero (3 $\cos^2 54.7°$−1=0) with mechanical rotation of the sample at 54.7° (the magic angle) with respect to the magnetic field (FIG. 7A), resulting in narrow NMR resonances.

Electron Dephased Rotational Echo DOuble Resonance (EDREDOR)

Rotational Echo DOuble Resonance (REDOR), correlates the amount of dephasing during a spin-echo to distances between nuclear spin pairs—the closer the "dephasing" spin is to the "observed" spin, the stronger the dephasing. Similarly, spins with larger gyromagnetic ratios yield more dephasing, enabling longer distance measurements up to about 12 Å for $^{19}F$-$^{13}C$ spin pairs. Electron spins have magnetic moments about 660 times larger than $^{19}F$ nuclear spins. These strong electron spins may be used to measure electron-nuclear distances on a protein out to about 50 Å.

Figure 3:
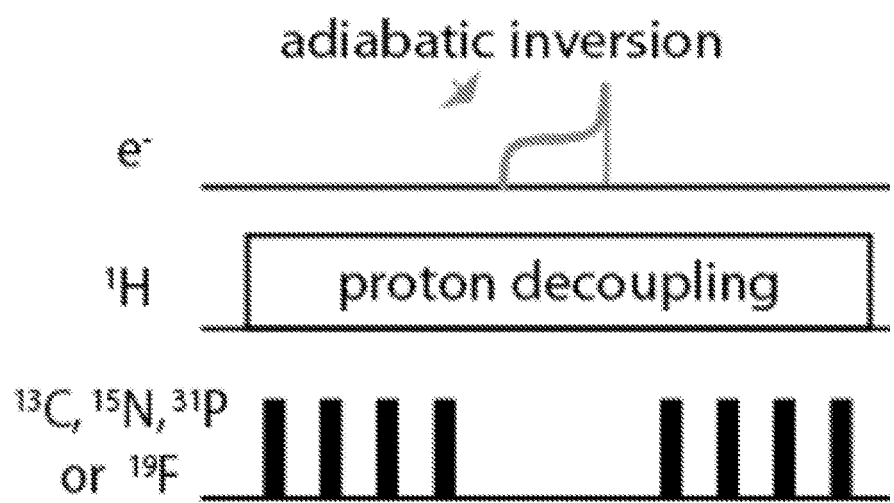
FIG. 3 is a pulse sequence for electron dephased REDOR.

The pulse sequence for such an Electron Dephased REDOR (ED-REDOR) experiment is shown in FIG. 3, which includes an adiabatic inversion of the electron spin only made possible with frequency agile gyrotron technology. In typical REDOR experiments, π pulses refocus magnetization, but in the experiment illustrated in FIG. 3, an adiabatic inversion on the electron spin interferes refocusing of the spin echo. The extent to which the magnetization is dephased directly encodes the electron-nuclear distance, and also the orientation of the dipolar vector. Similar to REDOR, ED-REDOR may also allow the measurement of the orientation of the electron-nuclear dipolar vector in addition to the measurement of the electron-nuclear distance.

Similar experiments exist in EPR, such as ENDOR (Electron Nuclear Double Resonance). EDREDOR is different in a few very important ways. Primarily, ED-REDOR is conducted during a MAS experiment that yields high resolution NMR spectra. The disadvantage to the MAS experiments is the lack of an EPR resonant structure—this is why frequency agile gyrotrons are so critical. Their high power levels compensate for the lack of EPR resonant structure, enabling an adiabatic inversion of the electron spins. Also, ENDOR is EPR detected, which limits the range of distance measurements to about 15 Å. ED-REDOR is also similar to solid state NMR structural measurements with paramagnetic relaxation effects. However, ED-REDOR has a $1/r^3$ distance dependence versus the $1/r^6$ dependence of EPRs, making it possible to measure out to about 50 Å rather than 15 Å.

One of the challenges to implementing ED-REDOR is extending the transverse electron relaxation to enable the adiabatic inversion, and longitudinal electron relaxation time to allow for the long mixing times required to measure long distances. This will be accomplished by cooling the sample to as low a temperature as possible. In one aspect, the sample may be cooled to a temperature below about 20 Kelvin.

Polarizing Agents and EPR Spin Labeled Proteins

Figure 13A:
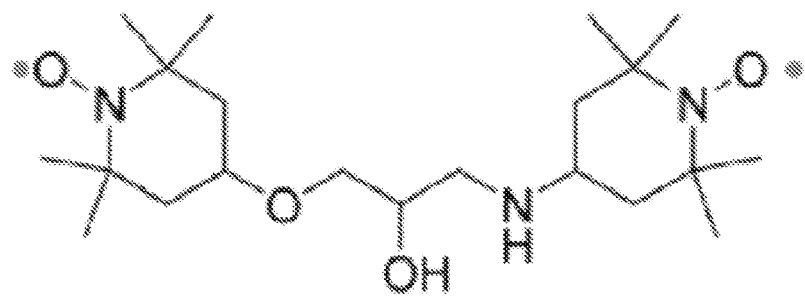
FIGS. 13A, 13B, and 13C illustrate exogenous (FIGS. 13A and 13B) and mounted EPR spins (FIG. 13C).

The stable organic radicals and EPR transition metals to be used for Cross Effect DNP, Solid Effect DNP, and electron-nuclear distance and dipolar orientation measurements have not previously been used for electron-decoupling or installing radicals on proteins for use with DNP because high power frequency agile gyrotrons and electron nuclear decoupling are needed. TOTAPOL (FIG. 13A) is an exogenous biradical polarizing agent comprised of two nitroxide moieties tethered together. The broad EPR lineshape and strong electron-electron dipolar coupling enabled by the frequency agile gyrotron is combination with TOTAPOL may yield efficient DNP with the Cross Effect. TOTAPOL is the currently the most common polarization agent used in magic angle spinning DNP, and may be used with in vivo studies. The broadbanded microwave irradiation from the frequency agile gyrotron as disclosed, which may cover the entire nitroxide lineshape, may enable powerful electron nuclear decoupling and distance measurements. In an aspect, more narrow line EPR moieties may also be used.

Figure 13B:
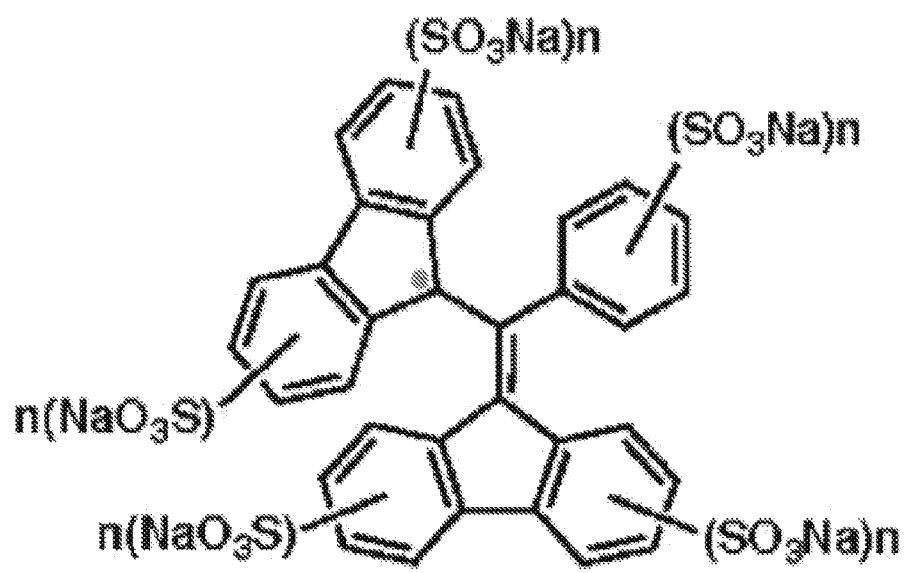
Figure 13C:
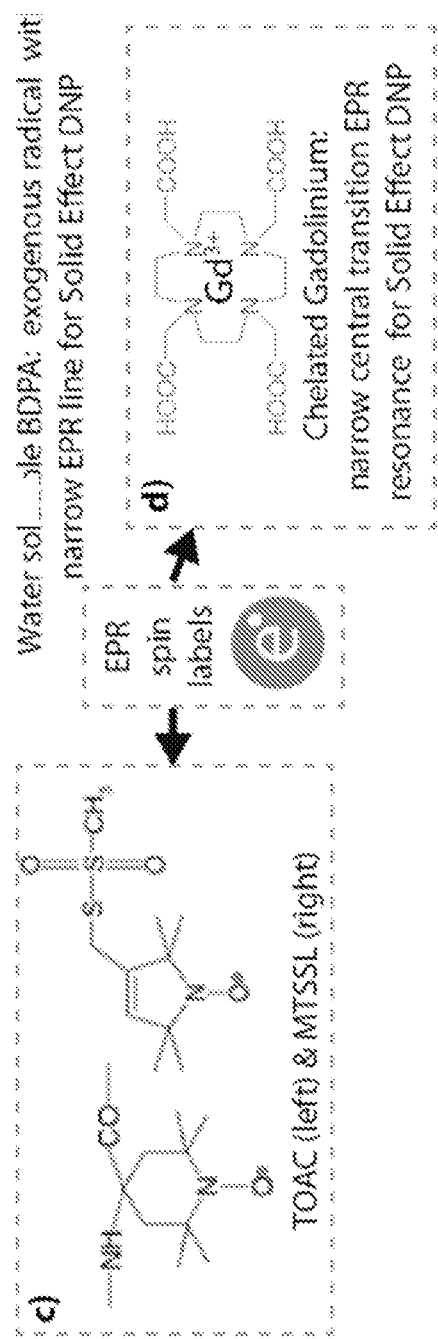

Narrow line EPR resonances like that in water-soluble BDPA (FIG. 13B) and gadolinium (FIG. 13C), are well-suited for Solid Effect DNP, especially when high electron nutation frequencies are available. The DNP enhancements from the Solid Effect still increase linearly with respect to microwave power, even when gB1=3 MHz. The 100 Watt power levels achieved by the frequency agile gyrotron as disclosed herein and EPR resonant structures may yield very high electron nutation frequencies in the range of about 5 MHz to about 30 MHz, or even higher.

Gadolinium is well-suited for Solid Effect DNP and electron nuclear decoupling for EPR spin labels on proteins. Although gadolinium has been used as a polarizing agent for DNP, and also been installed on proteins to make electron-electron measurements, performing DNP on a spin labeled protein has proven challenging. The narrow central EPR transition linewidth of gadolinium is dominated by isotropic zero-field splitting, which may simplify the implementation and data interpretation of electron nuclear distance measurements. However, the electron spin relaxation times of gadolinium are much shorter than nitroxides. Such fast relaxation makes it more challenging to manipulate these spins, especially to measure electron nuclear distances. Extreme sample cooling, in one aspect to temperatures of below about 15 Kelvin may enable combined gadolinium EPR and NMR.

TOAC (FIG. 13C) is a nitroxide amino acid incorporated with solid phase peptide synthesis (SPPS); its rigid conformation will lead to higher precision electronuclear measurements. MTSSL (FIG. 13C) may be installed onto cysteine residues, and may be used especially on protein GB1. As discussed previously, electron nuclear decoupling and collapsing the spin diffusion barrier may permit DNP at higher temperatures (about 220-273 K), where exquisite resolution in solid state NMR spectra of microcrystalline GB1 has been demonstrated.

Gyrotron and DNP Probe

A gyrotron, generally disclosed herein as 100 in FIG. 1, may be frequency agile and have a wide instantaneous bandwidth. The frequency agile gyrotron 100 may include an output window 104, an interaction cavity 106, and an electron gun 108. An electron beam 102 may extend through the length of the frequency agile gyrotron.

Figure 4E:
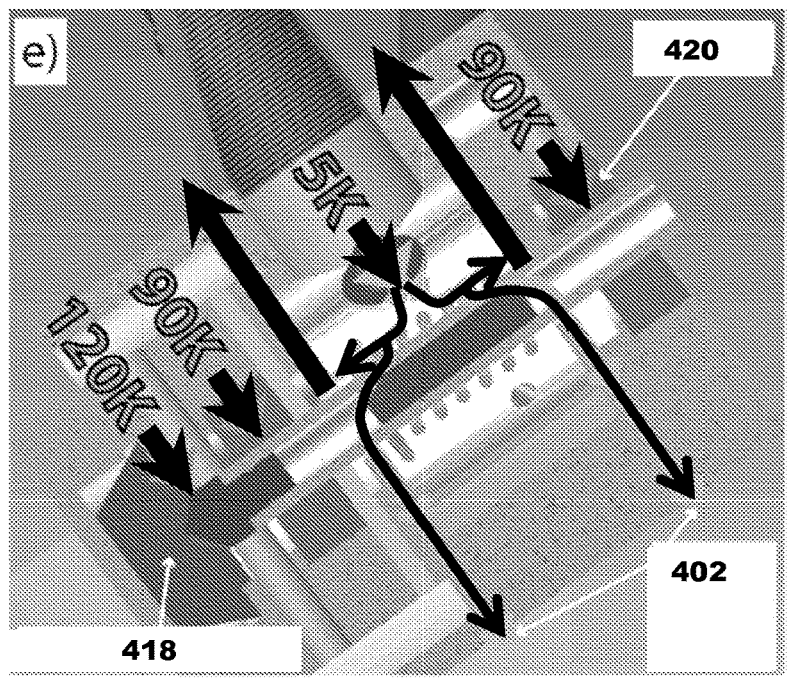
Figure 4F:
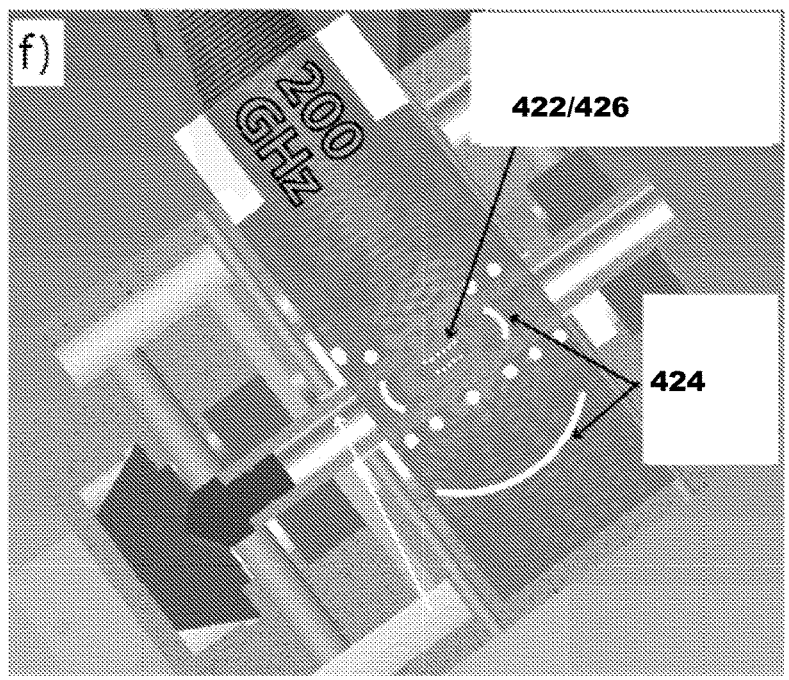
Figure 4G:
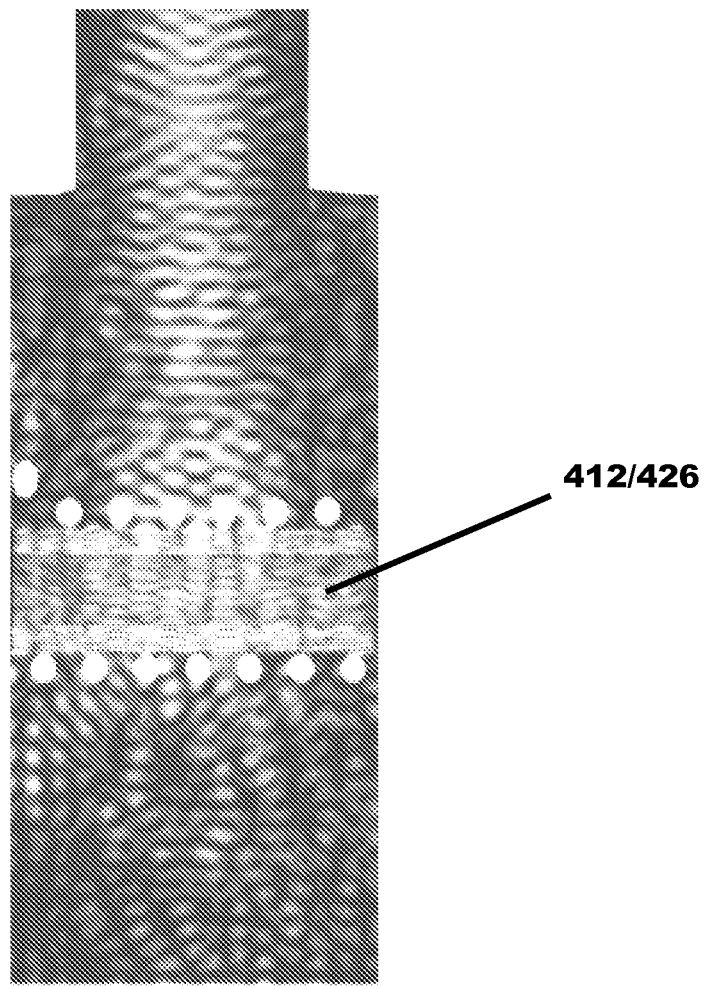
Figure 5A:
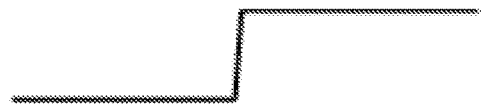
FIGS. 5A, 5B, 5C, 5D, 5E, and 5F are modulation schemes of the anode voltage accomplished with the circuit shown in FIG. 6.
Figure 5B:
Figure 5C:
Figure 5D:
Figure 5E:
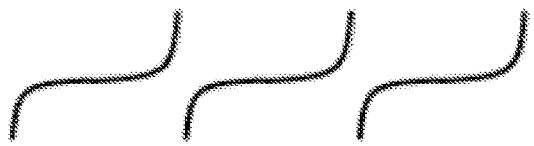
Figure 5F:
Figure 7:
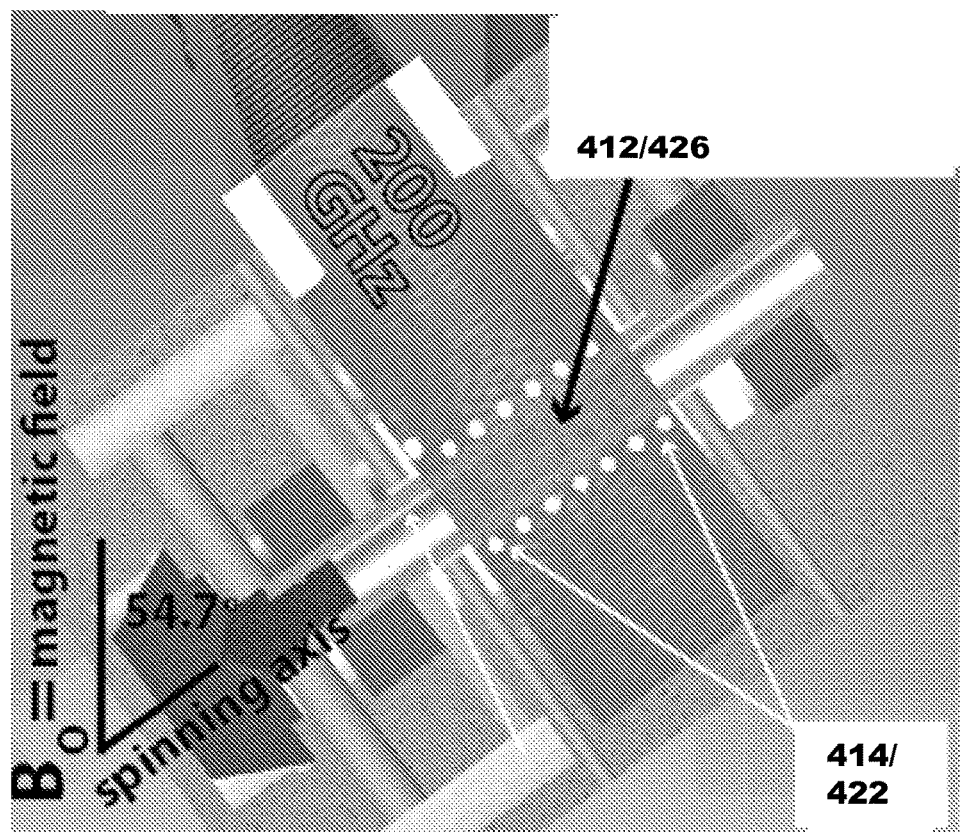
FIG. 7 is a simulation of a microwave electromagnetic field of the DNP sample chamber.

The frequency agile gyrotron 100 may be operatively connected to a NMR DNP probe 400. FIG. 4A is a schematic of a probe head for 300 MHz/200 GHz magic angle spinning DNP including a microwave waveguide 404 and vacuum jacketed cryogen lines 408, 410, which may be connected from the top of the magnet. FIG. 4B is a cross section showing the large sample volume 412 (about 250 µL) for in vivo and extremely high sensitivity in vitro studies. In an aspect, the DNP NMR probe may include a quadruple resonant NMR coil 414. FIG. 4C shows a DNP probe that includes a helium variable temperature line that cools samples to between about 25 Kelvin and about 27 Kelvin, a high-performance RF transmission line circuit 416, and an efficient microwave transmission line. FIG. 4D illustrates a vacuum jacketed Dewar 428 for 89 mm bore magnets with connection ports 430 to the top of the magnet. FIG. 4E is a schematic showing the cold helium gas flow along to rotor surface for efficient heat-exchange, then out exhaust ports 402 that establish a heat shield. The DNP probe may further include a drive cup (turbine) 418 and at least one bearing 420. FIG. 4F is an illustration of 200 GHz radiation in a DNP cavity including a microcoil 422 for about 1 µL samples 426. The microcoil 422 may provide improved EPR performance. Cross sections of the inductively coupled RF coils 422 and concave GHz mirrors 424 may generate about >1 MHz nutation fields on nuclear spin RF channels and >10 MHz nutation of electron spins resonating at about 200 GHz. FIG. 4G is a High Frequency Structure Simulation (HFSS) at 250 GHz of the sample chamber on the probe in FIG. 4C. FIG. 7 is a simulation of a microwave electromagnetic field of the DNP sample chamber 412/426.

Figure 10A:
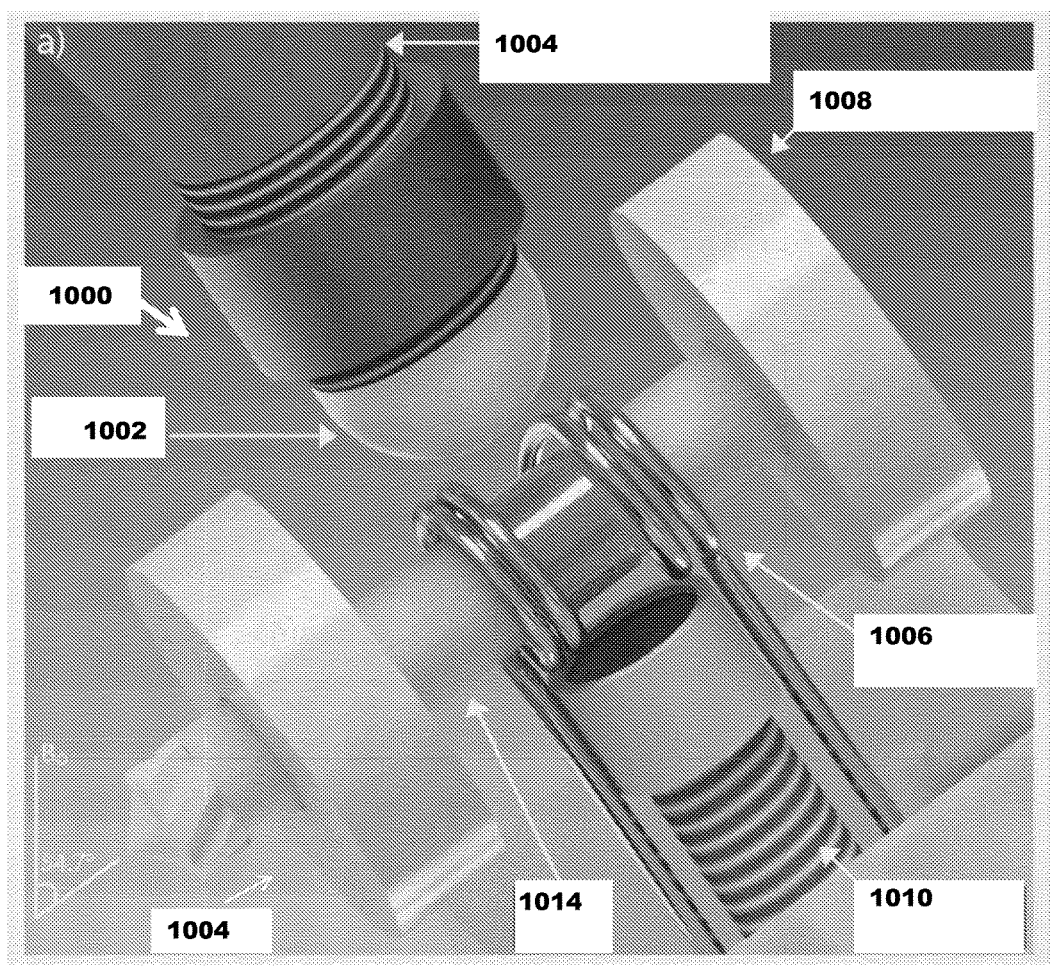
FIGS. 10A, 10B, and 10C are illustrations of a Fabry-Perot EPR resonator for magic angle spinning DNP.
Figure 10B:
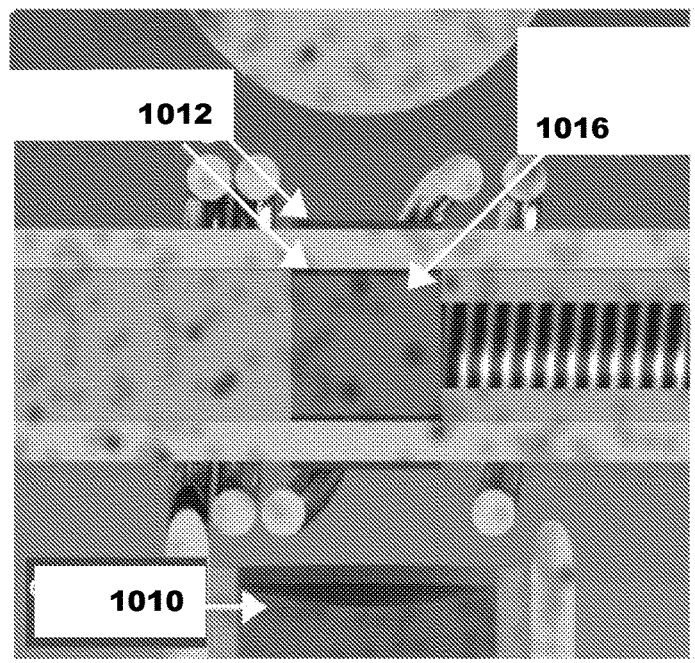
Figure 10C:
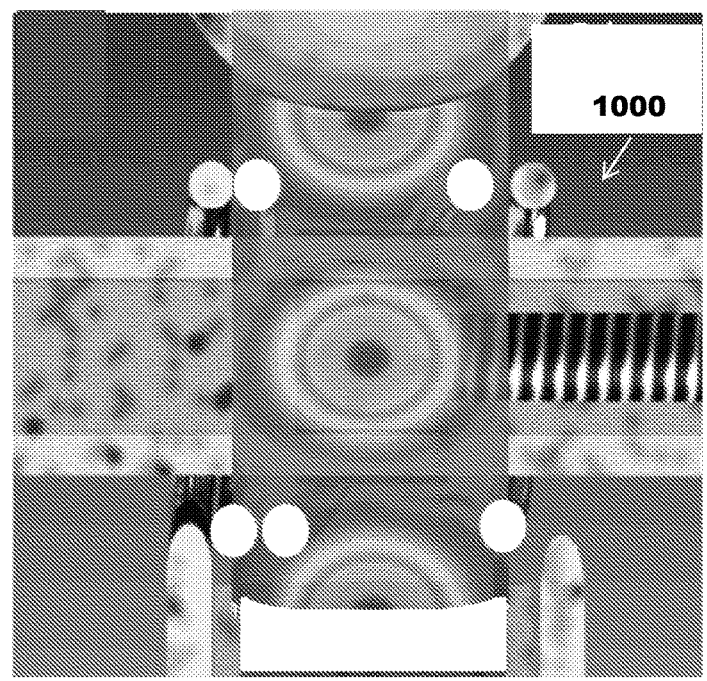

FIG. 10A is a schematic of a Fabry-Perot EPR resonator 1000 for magic angle spinning DNP. The resonator 1000 may include a magic angle spinning $N_2$ (g) bearing 1008 and a sapphire rotor 1014. FIG. 10A illustrates a Teflon lens 1002 that focuses the microwave power from the gyrotron 100 to the sample 1016 using a corrugated waveguide 1004 in between turns of the radio-frequency coil 1006. An adjustable copper mirror 1010 may excite the cavity mode. FIG. 10B illustrates the dielectric constants (impedance) of the sample 1016 and sapphire rotor 1014 are matched with anti-reflective THz coatings 1012 to reduce loss. FIG. 10C illustrates the cavity mode establishes a microwave field over the sample 1016.

The broadband microwave irradiation generated from the frequency agile gyrotron 100 may allow significantly more control over the DNP Hamiltonian. Beneficial hyperfine interactions may be able to be turned on and detrimental ones turned off to obtain significantly more sensitive and precise biomolecular structural refinement. For instance, electron decoupling may be implemented, which is analogous to proton decoupling and electron-nuclear distance measurements that are analogous to nuclear-nuclear measurements.

Figure 8C:
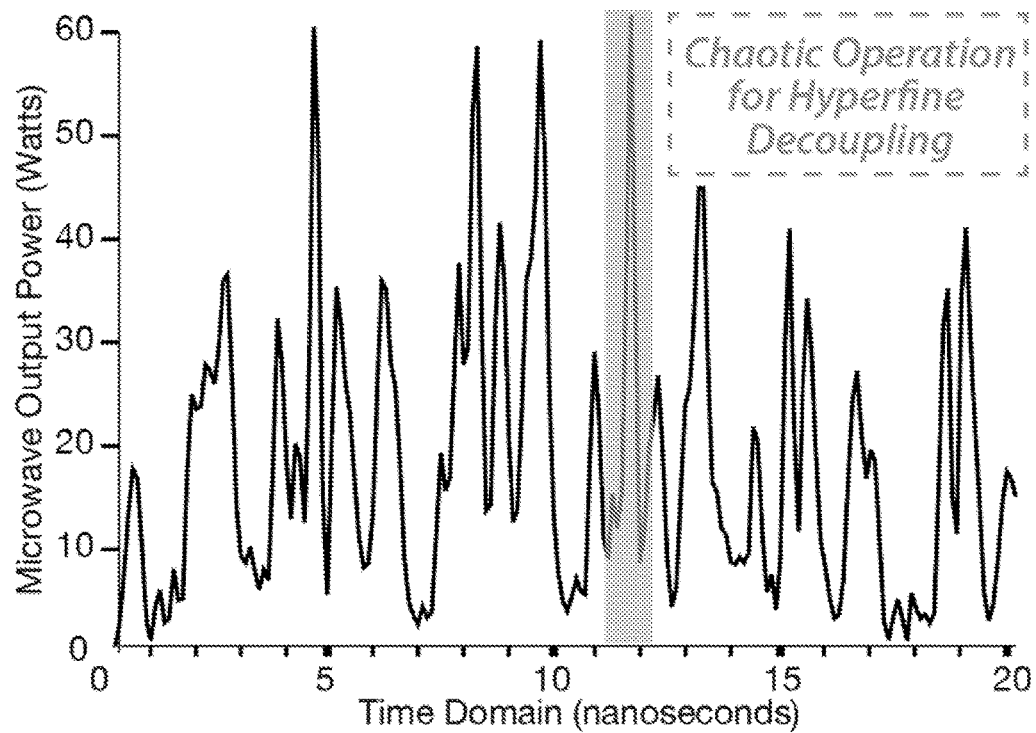
FIG. 8C is a graph of the chaotic operation of the gyrotron used for hyperfine decoupling.

The electron beam 102 ejected from cathodes in the frequency agile gyrotron 100 may generate microwave power that can interact with EPR spins at about 197 GHz. In the frequency agile gyrotron 100, the electron acceleration voltage between the cathode and anode determines the microwave output and may be changed quickly to permit electron nuclear decoupling (FIGS. 8A, 8B, and 8C). For instance, a frequency jump of about 300 MHz to switch from the DNP transfer condition to direct irradiation of the EPR resonances for decoupling may be achieved by decreasing the operating voltage of the gyrotron by about 670 V.

Figure 12A:
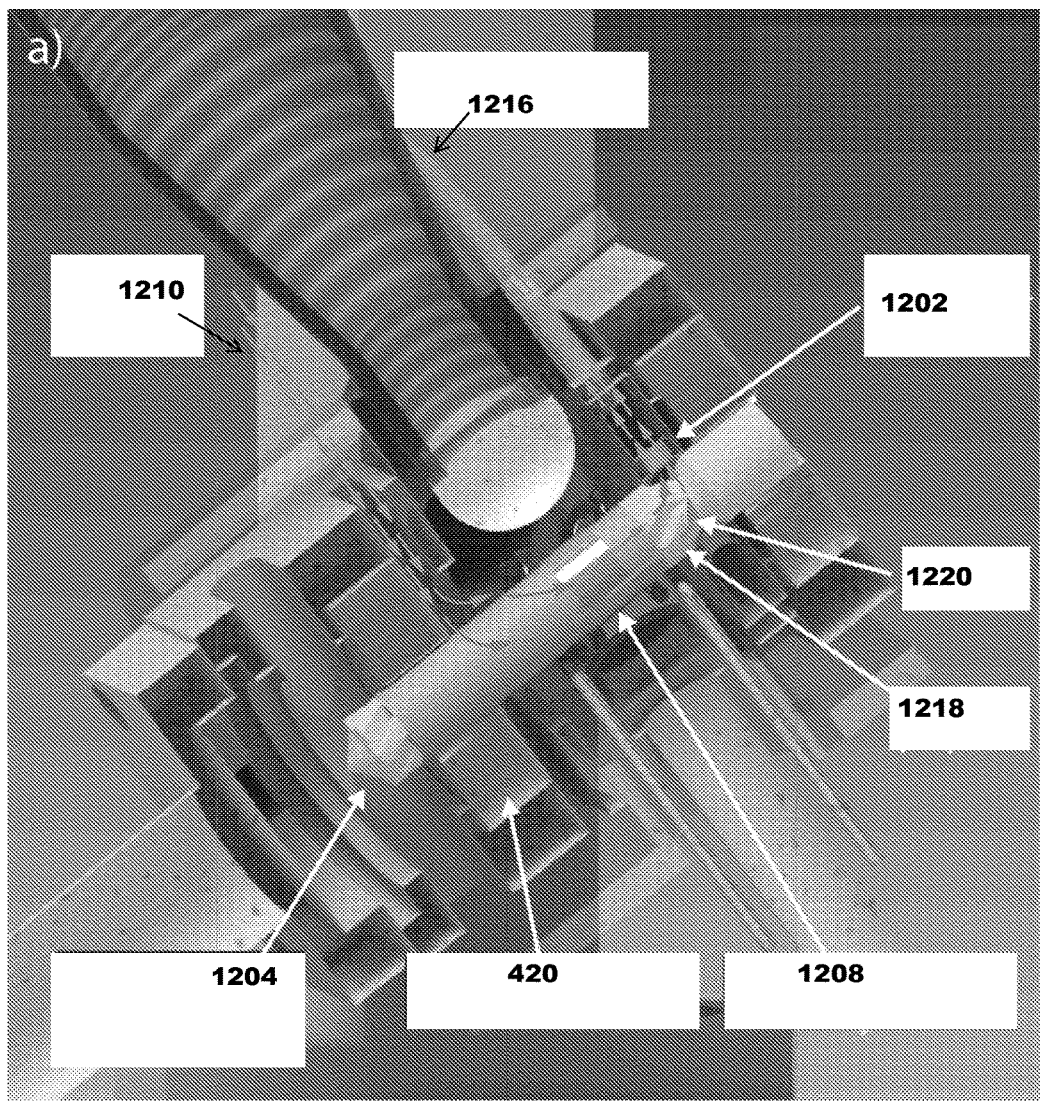
FIGS. 12A and 12B are illustrations of a miniature MAS rotor-driven helium recirculation system.

The about 5 Kelvin helium gas flow indicated by the arrows in FIG. 12A may effectively cool the sample 1208 while a bearing 420 fed with cold nitrogen gas (about 60 K) provides stable magic angle spinning. In an aspect, the sample 1208 may be at about 20 Kelvin. This design employs helium exhaust ports 402 (see FIG. 12B) that force the helium to be in extended contact with the NMR rotor to increase heat exchange efficiency, and also to cool heat shields surrounding the sample 1208. The system may further include ports 1222 (see FIG. 12B) for sample ejection, MAS bearing, MAS drive, helium cooling, and 200 GHz channel. The drive-tip 1204 (see FIG. 12A) and pressurized $N_2$ (g) turbine power may provide the centrifugal force to compress helium. The arrows in FIG. 12A indicate helium flow and expansive cooling of the sample 1208 followed by compression. The helium may flow to a miniature heat exchanger where heat is exchanged with a second closed helium loop cooled by a cryogenic refrigerator. In an aspect, the helium may flow from a refrigerator 1214, to a heat exchanger for re-cooling 1216, from the heat exchanger 1210, and return to the refrigerator for re-cooling 1212. A helium propeller 1218 and a helium impeller 1220 may be used to move the helium through the system, as illustrated in FIG. 12A.

Figure 8D:
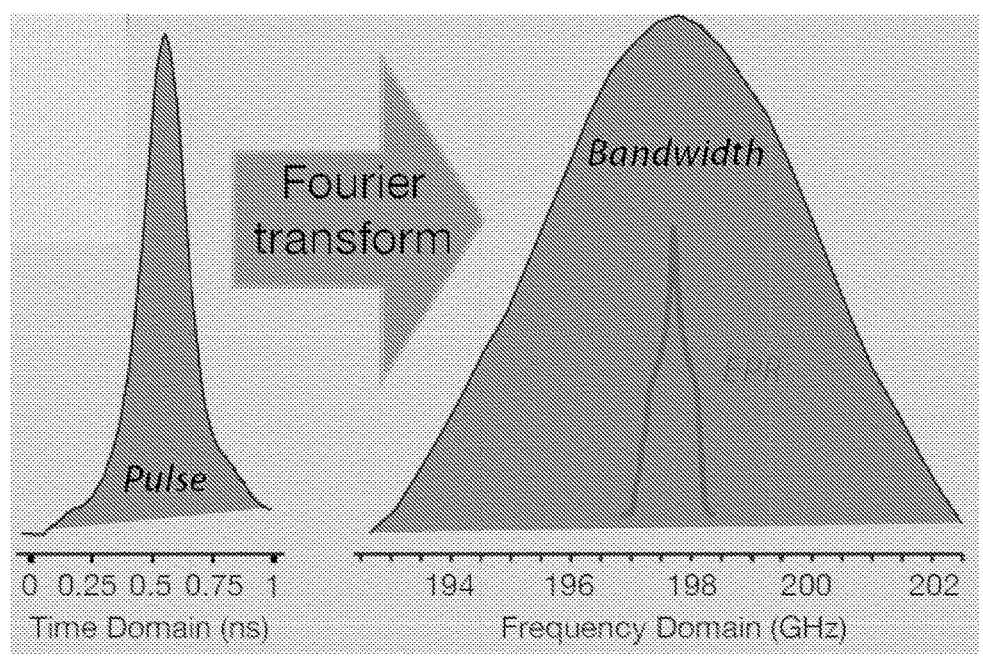
FIG. 8D shows the expansion of the highlighted time points in FIG. 8C showing instantaneous microwave bandwidth is much wider than the nitroxide EPR linewidth.

In the frequency agile gyrotron as disclosed herein, the operational voltage determines the microwave output frequency. In an aspect, the voltage-tunable gyrotron may change the frequency by about 1 GHz in about 1 second. The frequency agile gyrotron may allow for much faster voltage control and adiabatic inversions through the about 1 GHz nitroxide lineshape in about 2 µs. In an aspect, the gyrotron may operate in a "chaotic" mode of operation for hyperfine decoupling. The physics of the interaction of the electron beam with the interaction cavity is shown in FIG. 8C. The gyrotron quickly switches between axial modes resulting in short (<1 ns) pseudo-random pulses that are excellent for hyperfine decoupling. In an aspect, the instantaneous bandwidth of the 200 picosecond pulse in FIG. 8D may be about 4 GHz and may completely cover the 1 GHz nitroxide lineshape.

To perform NMR experiments relevant to biomolecular structure determination with DNP, probe instrumentation may perform a diverse set of tasks including; control of nuclear spins with efficient multiresonant RF circuits, control of EPR spins with GHz irradiation using waveguide and quasioptics, and cryogenic cooling with stable about 5 KHz to about 8 KHz magic angle spinning. Spinning at the magic angle (54.7°) averages anisotropic interactions in the Hamiltonian and results in narrow NMR resonances and resolved spectra. The high-performance quadruple resonance NMR DNP probes must retain the capability to implement all of the homo and heteronuclear polarization transfer and decoupling schemes that are integral to solid-state NMR spectroscopists.

RF transmission line circuits may generate about 83 KHz nutation frequencies on multiple RF channels and may be employed for rotors up to 7 mm diameter with sample volumes of up to 250 μL (FIG. 4A, 4B, 4E, 4G). Most DNP probes typically have about 30 μL sample volumes. The new DNP probe accommodating larger rotors will enable improved sensitivity for in vivo samples.

Sometimes it may be prohibitively difficult to make such large sample volumes of isotopically labeled protein and drugs. Therefore, inductively coupled microcoils that house sample volumes of about 1 μL may be incorporated into the DNP probes in an aspect. In addition to achieving excellent filling factors and sensitivity with 1 μL sample volumes, there are many additional advantages to microcoils from a RF and GHz perspective.

Challenges to achieving high quality EPR resonators in MAS include coupling the microwave power efficiently into the sample, and addressing losses of microwave power from the lossy sample. The system in FIG. 4F accomplishes both of these. Concave mirrors 424 placed in the rotor itself and opposite the waveguide aperture focus the microwave power into the sample 426. A 1 μL sample, although lossy, is small compared to the large size of the EPR resonant structure, leading to high quality factors. Together with the high power levels achieved by the frequency agile gyrotrons disclosed herein, EPR quality factors of 5 to 80, corresponding to electron nutation frequencies of 8-32 MHz may be achieved. Such strong control of the electron spins may lead to tremendous advancements in magnetic resonance methods.

Microcoils may also generate very high nutation frequencies of the nuclear spins. With the high power amplifiers already in place on the spectrometer, high efficiency RF transmission line circuits, and microcoils, 0.1-1 MHz nutation frequencies may be generated on $^1H$, $^{19}F$, $^{31}P$, $^{13}C$, $^{15}N$, $^2H$; all simultaneously. Not all of the NMR pulse sequences may make use of all of these channels in the same experiment. In an aspect, the $^1H$ channel may be used for cross polarization and $^1H$ decoupling and the $^{19}F$ and $^2H$ channels may manipulate isotopically labeled spins on bryostatin. In addition, the $^{31}P$ channel may control $^{31}P$ spins on phospholipid head groups and phosphorylated tyrosine residues in the active site of a protein. Correlations between $^{13}C$ and $^{15}N$ on uniformly labeled proteins between the $^{19}F$, $^2H$, and $^{31}P$ spins may yield not only distance constraints, but also, spectral filtering to clear-up spectral congestion. For site-resolved spectra of fully labeled proteins of >400 amino acids using $^{13}C$ and $^{15}N$, uniquely resolved spins and advance probe technology as described herein may be utilized. Building instrumentation that can manipulate seven types of spins (including the electron spins) simultaneously represents a huge leap forward in innovation from typical solid state NMR probes that are triple resonance.

Among the challenges to achieving high quality EPR resonators in MAS experiments of >5 Tesla include coupling the microwave power efficiently into the sample, and overcoming losses of microwave power in the resonator. The Fabry-Perot resonance structure 1000 shown in FIGS. 10A, 10B, and 10C accomplishes both of these objectives. An adjustable Teflon lens 1002 couples the 200 GHz microwave power 1004 from the gyrotron 100 efficiently into the EPR resonator 1000 through a split radio-frequency coil 1006 design. An adjustable concave copper mirror 1010 optimizes the boundary condition to excite a strong cavity mode (FIG. 10C). Anti-reflective coatings 1012, and a sapphire sample rotor 1014 minimize loss of power when the microwaves pass through materials with different dielectric constants (FIG. 10B). A High Frequency Structure Simulator may be used to calculate the propagation of the microwaves and optimize the materials and geometry in the EPR resonator. High quality factors (Q~100) can be achieved because the lossy sample 1016 is small compared to the size of the EPR resonant structure 1000. There are no EPR resonators currently available for high-frequency MAS DNP; the EPR quality factor of existing instrumentation is Q~1.

Efficient Helium Cooled Magic Angle Spinning

Enhanced sensitivity in magnetic resonance is available at cryogenic temperature due to a 1/T dependence of the spin polarization (see Eqn. (I)). Electron and nuclear spin relaxation times also increase drastically at lower temperatures, permitting efficient transfers of the enhanced electron polarization to nuclear spins. Consequently, most MAS DNP experiments are performed at 80-100 Kelvin where inexpensive $N_2$ (g) can be used both to spin the NMR sample and to provide cooling. There are some initial studies that use about 6 L/hr of liquid helium to cool samples to about 25 K, but are encumbered by the ever-increasing high cost of helium. Current efforts to recycle the helium entail a tremendous investment in infrastructure and laboratory space (see FIG. 11, bottom).

Figure 11:
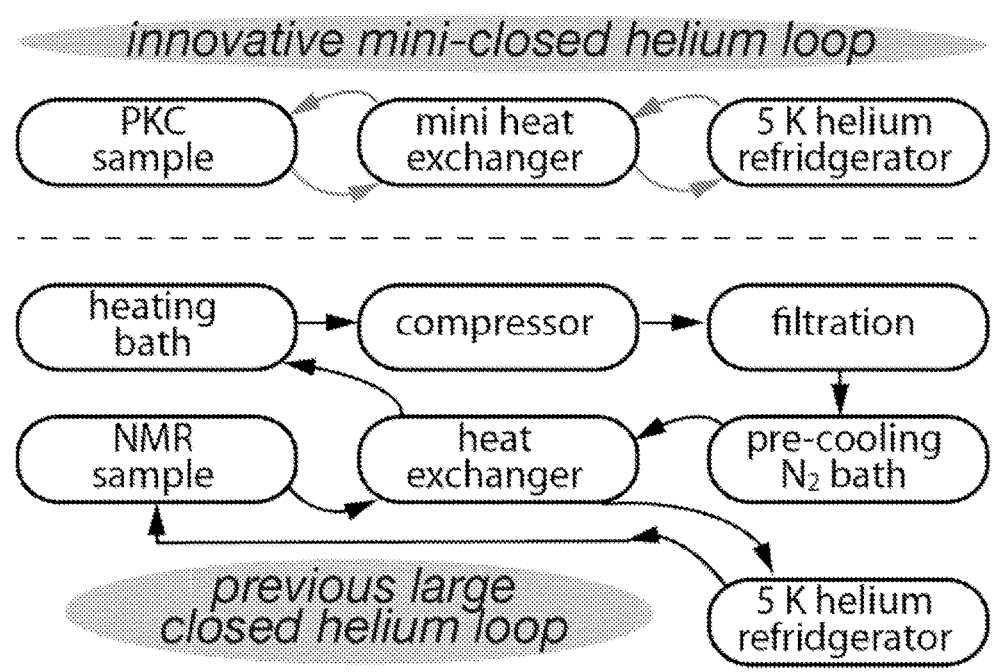
FIG. 11 is a schematic of a miniaturization of helium recirculation for cryogenic MAS DNP that may reduce the cost and footprint of recycling helium and permit long-term operation at cryogenic temperatures of less than about 27 K.
Figure 12B:
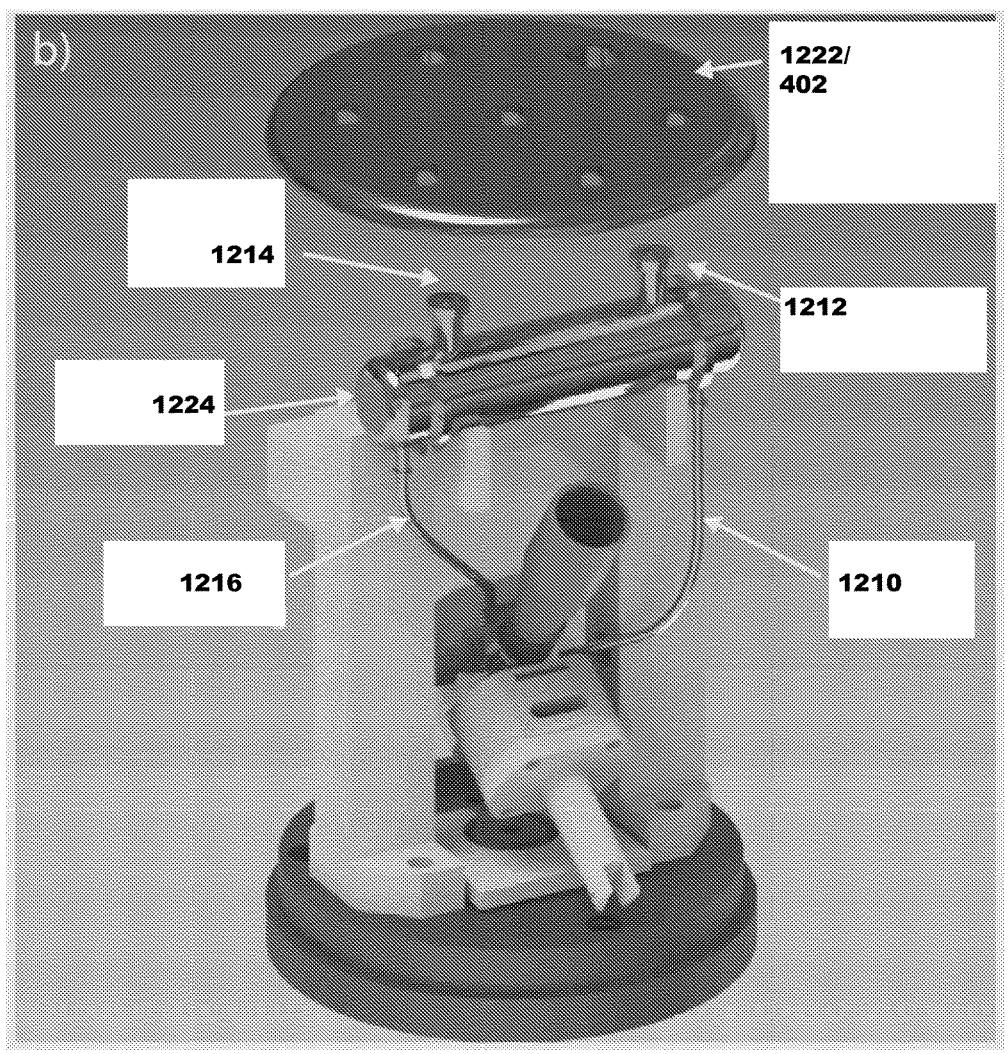

The frequency agile gyrotron system may further include a miniature helium recirculation system shown in FIG. 11 (top) and FIGS. 12A and 12B. A centrifugal compressor 1202 mounted on the rotor harnesses the rotational kinetic energy afforded by the drive-tip turbine 1204 (FIG. 12A) and about 8 kHz sample rotation. The helium may circulate between a miniature heat-exchanger 1226 and the sample 1208 (see FIGS. 12A and 12B). The helium flowing over the rotor may be cooled to about 5 K, but the sample may be about 25 K due to heat conduction along the rotor and microwave heating.

The geometry of the rotor fins and compression manifold may yield the flow pattern shown in FIG. 12. At field strengths of about 7 Tesla, a spin at about 8 KHz may yield narrow linewidths in the MAS NMR spectra. Vacuum jacketed insulation may be critical to separate the helium loop from the sample chamber 1208 maintained at 90 K with $N_2$ (g).

Previous experiments below 10 K required tens of liters of helium an hour. There has been a renewed interest in cold helium spinning in solid-state NMR the last decade, and the drive has been to make the cooling more efficient. The length of the rotor may be extended and tight disks (baffles) used to isolate the cold sample region in the center of the rotor. The helium gas flow indicated by the blue arrows in FIG. 4E may be used. This design employs helium exhaust ports 402 that force the helium to be in contact with the rotor much longer to increase heat exchange efficiency, and also to cool the disks surrounding the sample to establish a heat shield. These improvements, in addition to using about 100 Kelvin MAS spinning gases, may allow sample temperatures of less than about 20 Kelvin with minimal helium consumption. In an aspect, the helium consumption may be less than about 1 L/hr.

Spectrometer Control of the Gyrotron Frequency

Figure 6:
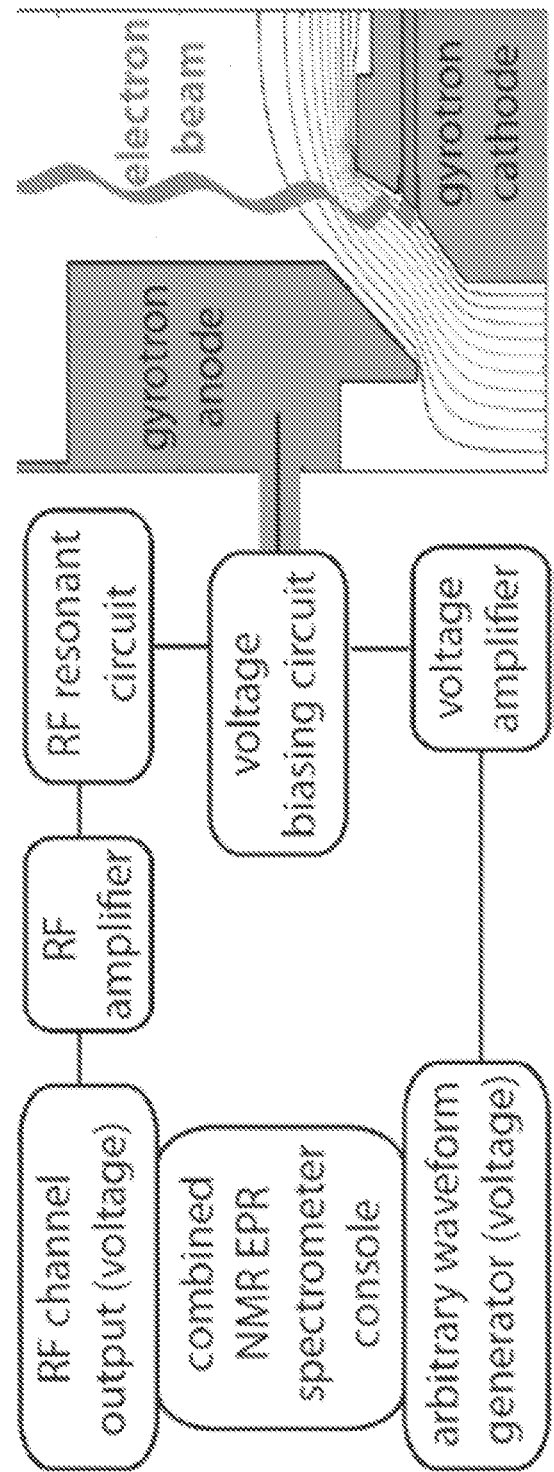
FIG. 6 is a scheme of a frequency control circuit of a gyrotron using an integrated NMR EPR spectrometer.

In tunable gyrotrons, the acceleration voltage between the cathode and anode in the magnetron injection gun dictates the microwave output frequency (see FIG. 9B, right). Control of the voltage (and frequency) of the gyrotron by the NMR spectrometer enables seamless integration between the NMR and EPR channels in DNP experiments. The TECMAG spectrometer may have extra arbitrary waveform generators with a 10 ns step size. Thus, implementing the voltage and frequency agility schemes shown in FIG. 6 may be accomplished from the integrated DNP spectrometer console. Voltage output channels from the spectrometer may be amplified (and optically isolated), added together in a biasing circuit, and connected to the gyrotron anode. The voltage on the anode controls the electric potential (see FIG. 6, right), thus tuning the velocity of the electron beam and the microwave frequency output.

Protein Sample Preparation for NMR

Previously, dozens of milligrams of protein for atomic level structural biology was required. In an aspect, the sample size for in vitro samples may be decreased. With the microcoil instrumentation and DNP sensitivity described previously herein, there may be excellent sensitivity with about 1 μL samples. For example, with about 200 μg of protein (most of the volume is taken up by lipids), a full-length protein in eukaryotic cells may be expressed and the functional kinase may be purified without need for optimizing yields at every step of the protocol. Similarly, 200 μg of a protein from solid phase peptide synthesis may enable incorporation of selectively isotopically labeled residues and EPR tags. At the same time, it will be much easier to provide about 30 μg of sample versus the 4 mg currently needed.

In vitro measurements may benefit from DNP sensitivity. For instance the sensitivity may be leveraged to determine drug and protein confirmations present at a minute fraction of the cryogenically trapped ensemble. Often these thermodynamically less favored states are critically the most important structures—excursions in the energy landscape that result in drug binding, dissociation, and catalysis.

EXAMPLES

Prophetic Example 1

FIG. 4B shows the chemical structure 1,3-bisdiphenylene-2-2-phenylallyl (water soluble BDPA), the exogenous stable organic radical that may be a source of the enhanced magnetic resonance polarization (sensitivity). FIG. 2A shows the electron paramagnetic (EPR) spectra of nitroxide and BDPA radicals in red. The enhancement profiles show the level of polarization enhancement obtained on the nuclear spins by sweeping the microwave irradiation frequency (or NMR magnet field strength) through the DNP matching conditions. For the narrow line BDPA radical, the Solid Effect, a two-spin DNP mechanism is active when the microwave irradiation frequency is 300 MHz (the proton nuclear Larmor frequency) away from the EPR resonance. Protons are polarized from the Solid Effect when the gyrotron is set to 197.0 GHz and the EPR resonance is at 197.3 GHz.

An in vitro NMR sample will contain about 200 micrograms of isotopically labeled bryostatin and also PKC C1b domain, phosphatidyl serine lipids, BDPA DNP polarizing agent, and a cryoprotecting matrix of glycerol. The sample will be loaded into a rotor for magic angle spinning (MAS). For in vivo ligand structural determination, about 400 mg of human cells (HeLa or similar) will be treated with isotopically labeled bryostatin, spun down, and then resuspended in a cryoprotecting glycerol matrix with dissolved DNP polarizing agent, before being centrifuged into a MAS NMR rotor.

Simultaneous radio frequency irradiation resonant with $^1$H, $^2$H, $^{31}$P, $^{13}$C, and $^{15}$N spins from a custom designed NMR radio frequency circuit may yield sufficient control of the nuclear spins to attenuate elements in the NMR Hamiltonian that lead to line broadening, while also permitting the measurement to sub-angstrom precision between $^{13}$C, $^{15}$N, $^2$H isotopic labels on bryostatin and $^{31}$P spins on the phospholipid head groups.

With the microcoil instrumentation and DNP sensitivity described previously herein, there may be excellent sensitivity with about 1 μL samples. For example, with about 200 μg of protein (most of the volume is taken up by lipids), a full-length protein in eukaryotic cells may be expressed and the functional kinase may be purified without spending a lot of time trying to optimize yields at every step of the protocol. Similarly, in a cost-effective manner, 200 μg PKC C1b domain from solid phase peptide synthesis will permit incorporation of selectively isotopically labeled residues and EPR tags. At the same time, it may be easier to provide about 30 μg of isotopically labeled bryostatin analogs versus the 4 mg currently needed.

In vivo NMR spectroscopy may ensure that the PKC is bound to endogenous lipids along with all of the co-factors, anchoring proteins, scaffold proteins, and other macromolecules present in the membrane that play a role in regulation. For these in vivo experiments, large 250 μL sample volumes may be used—it is not difficult to culture cells and spin them down in a centrifuge to get about 200 mg quantities; the tough part is always the purification, refolding, and reconstituting into lipids. The in vivo spectroscopy may be extended to primary cells and determine the structures of bryostatin and phorbol in diseased tissue.

Long-range distances will be measured between rigid nitroxide labels on the C1b domain and $^{13}$C labels both on residues in the binding pockets and on ligands with a ±0.2 Å precision.

The examples described herein are included to demonstrate preferred embodiments of the invention. It should be appreciated by those of skill in the art that the techniques disclosed in the examples included herein represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

What is claimed is:

1. A frequency agile gyrotron system for DNP (dynamic nuclear polarization) NMR (nuclear magnetic resonance) comprising:

an NMR spectrometer;

a signal processor operatively connected to the NMR spectrometer, wherein the signal processor receives one or more voltages from the NMR spectrometer and produces a control signal; and a frequency agile gyrotron operatively coupled to the NMR spectrometer and to the signal processor, the frequency agile gyrotron configured to emit a broad-banded microwave output comprising a gyrotron bandwidth;

wherein:

the NMR spectrometer controls a frequency of the broad-banded microwave output via the control signal, the frequency agile gyrotron responds to the control signal on a timescale of microseconds, and the gyrotron bandwidth is wider than an EPR (polarization of electron spins) linewidth and a NMR frequency.

2. The system of claim 1, wherein the gyrotron bandwidth of the frequency agile gyrotron is between 10 MHz and 1000 MHz.

3. The system of claim 1, wherein:

the NMR spectrometer further comprises a magnetron injection gun comprising a cathode and an anode; and the one or more voltages from the NMR spectrometer are chosen from at least one of: a cathode voltage, an anode voltage, and an acceleration voltage comprising a voltage difference between the cathode voltage and the anode voltage.

4. The system of claim 1, wherein the frequency agile gyrotron is operated as a backward wave oscillator.

5. The system of claim 1, wherein the frequency agile gyrotron produces the broad-banded microwave output at a phase and frequency stable condition.

6. The system of claim 5, wherein the broad-banded microwave output is sliced or gated to provide at least one of: a wide instantaneous bandwidth comprising short pulses on a nanosecond scale and an adjustable power transmission length for phase control.

7. The system of claim 1, wherein the NMR spectrometer further comprises a combined EPR-NMR magic angle spinning resonator.

8. The system of claim 1, further comprising a helium cooling system for cooling a sample to below 5 to about 60 Kelvin with helium using a spinning MAS (magic angle spinning) rotor as a centrifugal gas compressor.

9. A method of DNP (dynamic nuclear polarization) NMR (nuclear magnetic resonance) using a frequency agile gyrotron system comprising a NMR spectrometer operatively coupled to a frequency agile gyrotron, the method comprising controlling an output frequency of a broad-banded microwave output produced by the frequency agile gyrotron by changing an operational voltage of the frequency agile gyrotron in response to a control signal corresponding to at least one voltage received from a magnetron injection gun of the NMR spectrometer, the at least one voltage chosen from: a cathode voltage, an anode voltage, and an acceleration voltage comprising a voltage difference between the cathode voltage and the anode voltage.

10. The method of claim 9, wherein controlling the output frequency of the broad-banded microwave output produced by the frequency agile gyrotron comprises at least one of:

sweeping the output frequency on a timescale ranging from nanoseconds to microseconds;

producing the broad-banded microwave output in short pulses; and producing the broad-banded microwave output in a phase and frequency stable form and gating the broad-banded microwave output with at least one nanosecond scale switches.

11. The method of claim 9, further comprising at least one of:

performing at least one time-domain DNP transfer;

transferring polarization from electrons to a nucleus using hyperfine couplings of greater than 10 KHz;

decoupling an electron spin from a nuclear spin; and manipulating EPR (polarization of electron spins) spins during magic angle spinning NMR and EPR experiments to measure EPR to NMR distances and orientations.

12. The method of claim 11, wherein the operational voltage of the frequency agile gyrotron is changed on a timescale ranging from nanoseconds to microseconds to perform the at least one time-domain DNP transfer.

13. The method of claim 12, wherein the at least one time-domain DNP transfer is accomplished using at least one transfer mechanism chosen from: integrated solid effect, a nuclear orientation via electron spin locking, and an electron nuclear cross polarization.

14. The method of claim 9, further comprising cooling a sample to below 5 to 60 Kelvin with helium using a spinning MAS (magic angle spinning) rotor as a centrifugal gas compressor.

* * * * *